(12) United States Patent
Liu et al.

(10) Patent No.: US 7,834,179 B2
(45) Date of Patent: Nov. 16, 2010

(54) SPIROINDOLINONE DERIVATIVES

(75) Inventors: Jin-Jun Liu, Warren Township, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 322 days.

(21) Appl. No.: 12/101,206

(22) Filed: Apr. 11, 2008

(65) Prior Publication Data
US 2008/0293723 A1  Nov. 27, 2008

Related U.S. Application Data

(60) Provisional application No. 60/931,368, filed on May 23, 2007.

(51) Int. Cl.
*C07D 487/20* (2006.01)
*A61K 31/407* (2006.01)
*A61K 31/53* (2006.01)
*A61P 35/00* (2006.01)

(52) U.S. Cl. ..................... 544/184; 514/243
(58) Field of Classification Search .......... 544/184; 514/243
See application file for complete search history.

(56) References Cited

OTHER PUBLICATIONS

Wolff, Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
*J. Amer. Chem. Soc.*, (2005) vol. 127, p. 10130.
Chosez, L. et al, *Tetrahedron*, (1995) 11021-11042.
Ding et al, *J. Med. Chem.* (2006) 49:3432-3435.

* cited by examiner

*Primary Examiner*—Venkataraman Balasubramanian
(74) *Attorney, Agent, or Firm*—George W. Johnston; Patricia S. Rocha-Tramaloni

(57) ABSTRACT

There are provided spiroindolinone derivatives of the formula

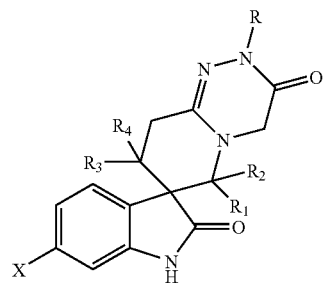

and pharmaceutically acceptable salts and esters thereof wherein $R_1$, $R_2$, $R_3$, $R_4$ and R are as herein described. The compounds exhibit anticancer activity.

8 Claims, No Drawings

SPIROINDOLINONE DERIVATIVES

PRIORITY TO RELATED APPLICATION(S)

This application claims the benefit of U.S. Provisional Application No. 60/931,368, filed May 23, 2007, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am. Chem. Soc., 2005, 127, 10130.

SUMMARY OF THE INVENTION

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention relates to spiroindolinone derivatives of the formula

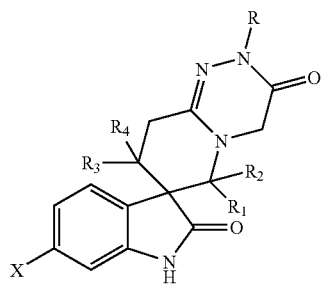

and pharmaceutically acceptable salts and esters thereof wherein $R_1$, $R_2$, $R_3$, $R_4$ and R are as herein described.

DETAILED DESCRIPTION OF THE INVENTION

The present invention relates to spiroindolinones of the formulas

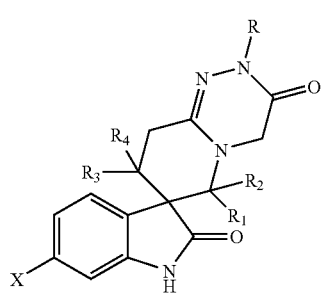

wherein

X is selected from the group consisting of hydrogen, halogen, cyano, nitro, ethynyl, cyclopropyl, methyl, ethyl, isopropyl, methoxy and vinyl, one of $R_1$ and $R_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, one of $R_3$ and $R_4$ is selected from the group consisting of lower alkyl, substituted lower alkyl lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, R is selected from the group consisting of hydrogen, lower alkyl and substituted lower alkyl and the pharmaceutically acceptable salts and esters thereof.

Preferred are compounds of formula I having a stereochemical structure shown as formula II

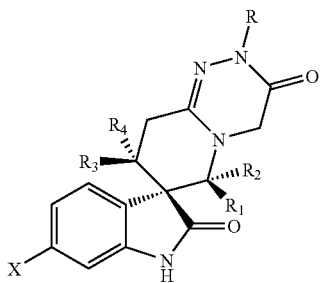

wherein
X is hydrogen, halogen, cyano, nitro, ethynyl, cyclopropyl, methyl, ethyl, isopropyl, methoxy, and vinyl,
$R_1$ is hydrogen,
$R_3$ is hydrogen,
$R_2/R_4$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl and
R is hydrogen, lower alkyl or substituted lower alkyl and the pharmaceutically acceptable salts and esters thereof.
Further preferred are compounds of formula II wherein
X is chorine or bromine,
$R_1$ is hydrogen,
$R_3$ is hydrogen,
$R_4$ is a substituted phenyl or substituted heteroaryl with the substituted phenyl or substituted heteroaryl selected from group consisting of:

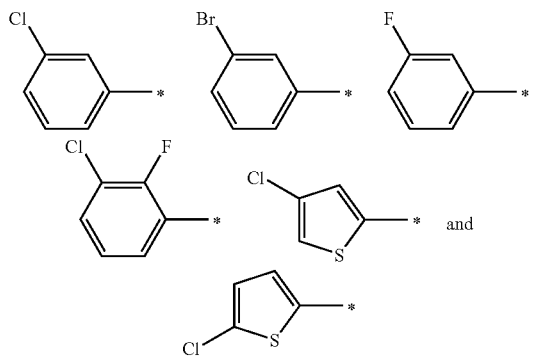

$R_2$ is independently selected from the group consisting of lower alkenyl, substituted lower alkenyl, aryl, substituted aryl, heteroaryl, substituted heteroaryl, cycloalkenyl and substituted cycloalkenyl and
R is hydrogen, lower alkyl or substituted lower alkyl.
Most preferred are compounds of the formulas
racemic (6'R, 3R, 8'S)-6-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione,
Chiral (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-8'-(3-chlorophenyl)-6'-(5-fluoro-2-methylphenyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione,
Chiral (6'R, 3R, 8'S)-6-chloro-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
Chiral (6'R, 3R, 8'S)-6-chloro-8'-(3-chlorophenyl)-6'-(1-methylene-propyl)-6',7',8',9'-tetrahydro spiro[3H-indole-3, 7'-(2H-pyrido[2,1-c][1,2,4]triazine)]-2, 3'(1H)-dione,
racemic (6'R, 3R, 8'S)-6-8'-(3-chlorophenyl)-2'-(3-dimethylaminopropyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-8'-(3-chlorophenyl)-2'-(2-methoxyethyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-2'-(2-acetoxyethyl)-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
Chiral (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-2'-(2-acetylaminoethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-8'-(3-chlorophenyl)-2'-(2-hydroxycarbonyl-methyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-8'-(3-chlorophenyl)-2'-(2-fluorocarbonyl-methyl)-6'-(1-methylene-propyl)-6',7',8',9'-tetrahydro spiro[3H-indole-3,7'-(2H-pyrido[2,1-c][1,2,4]triazine)]-2, 3'(1H)-dione,
racemic (6'R, 3R, 8'S)-6-chloro-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido[2,1-c][1,2,4]triazine)]-2, 3'(1H)-dione,
Chiral (6'R, 3R, 8'S)-6-chloro-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido [2,1-c][1,2,4]triazine)]-2, 3'(1H)-dione,
racemic (6'R, 3R, 8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2, 3'(1H)-dione,
Chiral (6'R, 3R, 8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido [2,1-c][1,2,4]triazine)]-2, 3'(1H)-dione,
racemic (6'R, 3R, 8'S)-2'-(2-aminocarbonyl-methyl)-6-chloro-8'-(3-chlorophenyl)-6'-(1-methylene-propyl)-6',7', 8',9'-tetrahydro spiro[3H-indole-3,7'-(2H-pyrido[2,1-c][1,2,4]triazine)]-2, 3'(1H)-dione, racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2, 3'(1H)-dione, racemic (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido[2,1-c][1,2,4]triazine)]-2, 3'(1H)-dione, racemic (6'R,3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido[2,1-c][1,2,4]triazine)]-2, 3'(1H)-dione, racemic (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2, 3'(1H)-dione, Chiral (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2, 3'(1H)-dione, racemic (6'R, 3R, 8'S)-6-chloro-8'-(3-chlorophenyl)-6'-isopropenyl-6',7',8',9'-tetrahydro spiro[3H-indole-3,7'-(2H-pyrido[2,1-c][1,2,4]triazine)]-2, 3'(1H)-dione, racemic (6'S, 3R, 8'R)-6-chloro-8'-(3-chlorophenyl)-6'-isopropenyl-6',7',8',9'-tetrahydro spiro[3H-indole-3,7'-(2H-pyrido[2,1-c][1,2,4]triazine)]-2, 3'(1H)-dione, racemic (6'R, 3R, 8'S)-6'-(2-allyloxy-5-iodo-phenyl)-6-chloro-8'-(3-chlorophenyl)-2'-methyl-6',7',8',9'-tetrahydro spiro[3H-indole-3,7'-(2H-pyrido[2,1-c][1,2,4]triazine)]-2, 3'(1H)-dione, racemic (6'R, 3R, 8'S)-6-8'-(3-chlorophenyl)-6'-(5-ethynyl-2-hydroxy-phenyl)-2'-methyl-6',7',8',9'-tetrahydro spiro [3H-indole-3,7'-(2H-pyrido[2,1-c][1,2,4]triazine)]-2, 3'(1H)-dion, racemic (6'R, 3R, 8'S)-6-chloro-8'-(3-chlorophenyl)-6'-[2-(2,3-dihydroxy-propoxy)-5-iodo-phenyl)-2'-methyl-6',7',8',9'-tetrahydro spiro[3H-indole-3,7'-(2H-pyrido[2,1-c][1,2,4]triazine)]-2, 3'(1H)-dione and racemic (6'S, 3R, 8'S)-6-chloro-8'-(3-chlorophenyl)-6'-[2-(2,3-dihydroxy-propoxy)-5-ethynyl-phenyl)-2'-methyl-6',7',8',9'-tetrahydro spiro[3H-indole-3,7'-(2H-pyrido[2,1-c][1,2,4]triazine)]-2, 3'(1H)-dione.

In the specification where indicated the various substituent groups (R values) may be substituted by 1-5 or, preferably, 1-3 substituents independently selected from the group consisting of lower alkyl lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

By the term "cycloalkenyl" is intended to refer to any stable monocyclic or polycyclic system which consists of carbon atoms only, with at least one ring thereof being partially unsaturated.

Examples of cycloalkenyls include, but are not limited to, cyclopentenyl or cyclohexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid hydroiodic acid, sulfuric acid, sulfamic acid, phosphoric acid and nitric acid, and those derived from organic acids such as p-toluenesulfonic acid, salicylic acid methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formulas I or II as well as their salts have at least one asymmetric carbon atom and therefore may be present as racemic mixtures or different stereoisomers. The various isomers can be isolated by known separation methods, e.g. chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formulas I or II having a carboxyl group or hydroxy group, which esters retain the biological effectiveness and properties of the compounds of formulas I and are cleaved in vivo (in the organism) to the corresponding active carboxylic acid or alcohol respectively.

Synthesis

Compounds of this invention in formula I or II can be synthesized according to the following general schemes. It will be readily apparent to those of ordinary skill in the art that compounds in formula I-II can be prepared by substitution of the reagents or agents in the general synthesis routes. The starting materials are either commercially available or can be synthesized by well-established literature methods known to those of ordinary skill in the art. Using purification by chiral chromatography, compounds in formula II can be obtained as an optically pure or enriched enantiomers.

Scheme 1

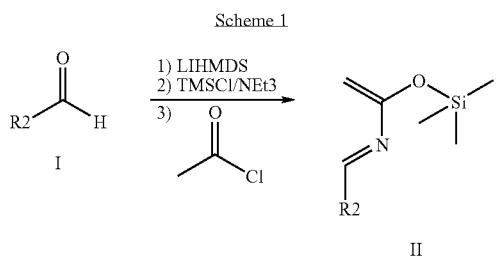

In general an appropriately selected aldehyde I can be reacted with lithium hexamethyldisilamide, chlorotrialkylsilane and acetyl chloride in a one-pot, multi-steps manner to generate 2-aza-1,3-butadiene II (Scheme I) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

Scheme 2

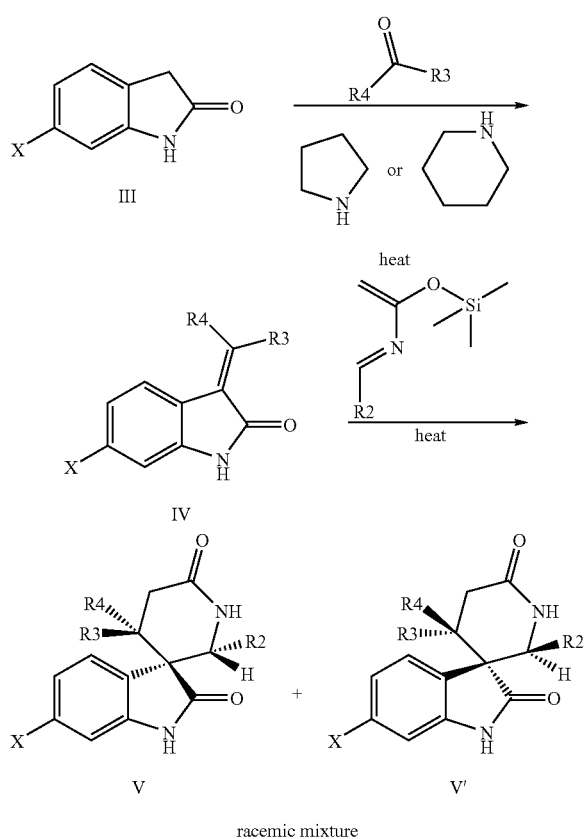

racemic mixture

Oxindole III can be reacted with an appropriately substituted aldehyde or ketone in the presence of base under heated condition in either a protic like methanol, ethanol or an aprotic solvent like toluene, o-xylene to give intermediate IV. The commonly used base is either pyrrolidine or piperidine. Intermediate IV can then be reacted with 2-aza-1,3-butadiene II in toluene or o-xylene under heating from 110° C. to 160° C. and anhydrous condition to afford a racemic mixture of siproindolinone V and V' as the major products as shown together with other minor stereoisomers. 6-substituted oxindole III starting materials are either commercially available or prepared according to literature methods, for examples, Kraynack, E. A.; Dalgrd, J. E.; Gaeta, F. C. A. *Tetrahedron Letters*, 1998, 39, 7679-7682. (Scheme 2).

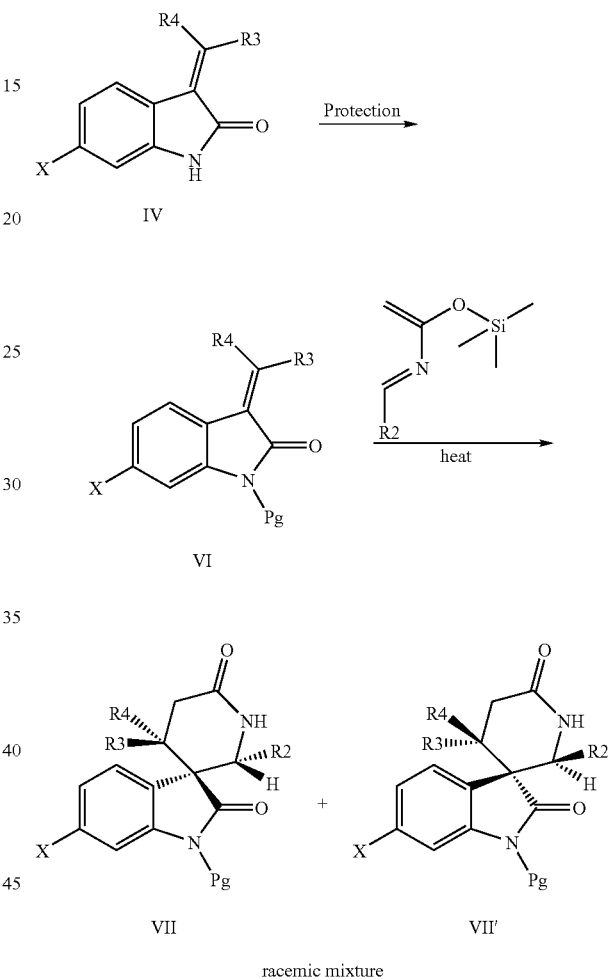

racemic mixture

Intermediate IV can be protected to give intermediate VI. The protective group can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc. In a similar manner intermediate VI can be reacted with a selected 2-aza-butadiene II prepared in Scheme 1 in toluene or o-xylene under heating from 110° C. to 160° C. and anhydrous condition to form intermediate VII and VII' as the major products shown as a racemic mixture of two enantiomers together with other minor stereoisomers (Scheme 3). Racemic mixture of V and V' or VII and VII' can be readily resolved into two chiral enantiomers by chiral Super Fluid Chromatography (SFC) or chiral HPLC or chiral column chromatography separation to give the two chiral enantiomers V can be selectively protected to give VII under controlled conditions. In this case, a useful protective group Pg here can be ethyl carbamate, or tert-butyl carbamate (BOC) (Scheme 4). The protective group can be attached by using ethyl chloroformate, or di-tert-butyl dicarbonate, and a base like 4-(dimethylamine)pyridine (DMAP) in dichloromethane at room or lowered temperature similar to the transformation from IV to VI in Scheme 3.

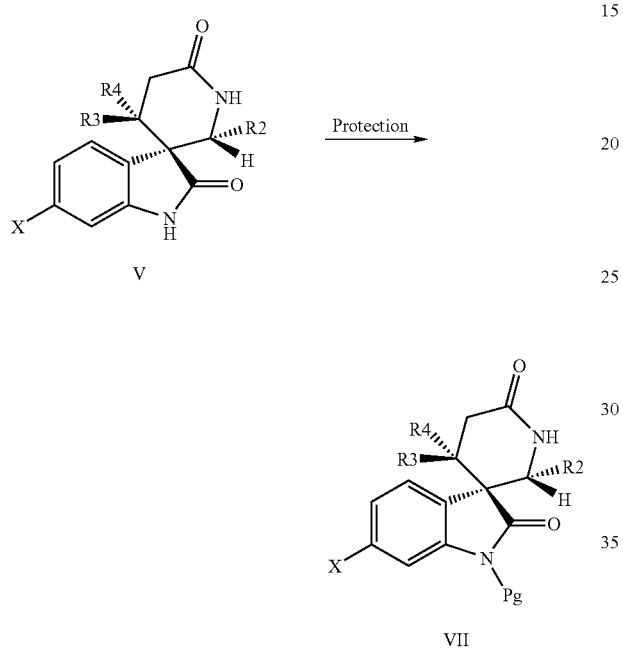

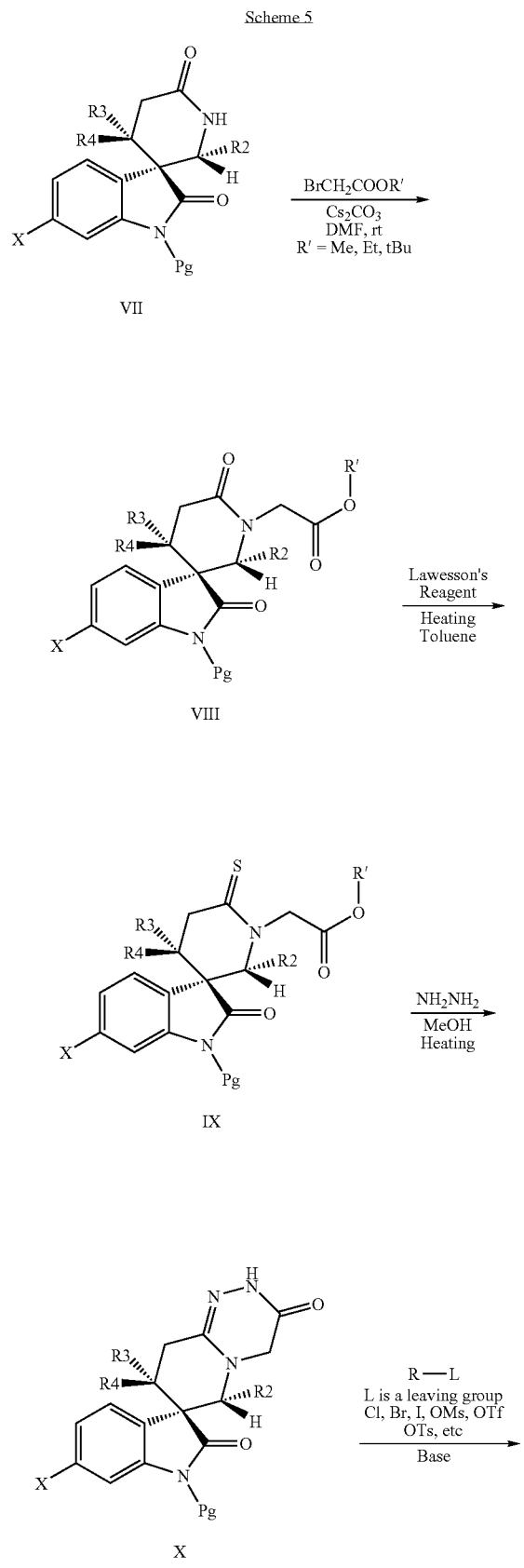

Synthesis of triazinone XII is described in Scheme 5. By using either an organic base or an inorganic base like Cs$_2$CO$_3$, LiH or NaH, and commercially available reagent alkyl bromoacetate (BrCH$_2$COOR', R'=Me, Et, tBu), N-alkylate intermediate VIII can be prepared from VII in good yield. A subsequent reaction to selectively convert lactam carbonyl to thiocarbonyl by Lawesson's reagent in toluene under heating condition affords intermediate IX in high yield. Treatment of IX with hydrazine monohydrate or anhydrous hydrazine in methanol in a sealed tube under heated condition leads to intermediate X. Alkylating reagent R-L and a base like LiH or NaH can be used to convert X into intermediate XI. R is a lower alkyl substituted lower alkyl, lower cycloalkyl, substituted lower cycloalkyl group. L is a good leaving group such as Cl, Br, I, OMs, OTf, OTs, etc. In these transformations from VII to XI, a useful Pg group is trimethylsiloxyethoxymethyl (SEM). Trimethylsiloxyethoxymethyl (SEM) group can be removed by a deprotection reaction in a two-step manner to form compounds XII of formula II: 1) trifluoroacetic acid in dichloromethane at room temperature; 2) Hunig base (iPr$_2$NEt) in methanol under heating condition (100° C.).

-continued

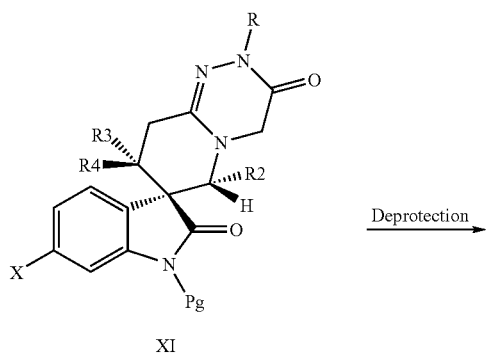

XI

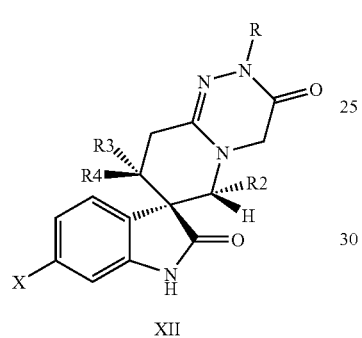

XII

When R$_2$ is selected from phenyl group substituted with ethynyl, 1-propynyl, alternative synthetic methods can be used to gain access to compounds XII-b Typically, the analogues XII-a with corresponding Iodo- or bromo-substituted phenyl R$_2$ are prepared first according to the methods in scheme 1-5, followed by a catalytic palladium mediated Sonogashira reaction to give those XII-b with a R$_2$ as the corresponding phenyl substituted with ethynyl or other substituted alkynyl group. (Scheme 6).

Scheme 6

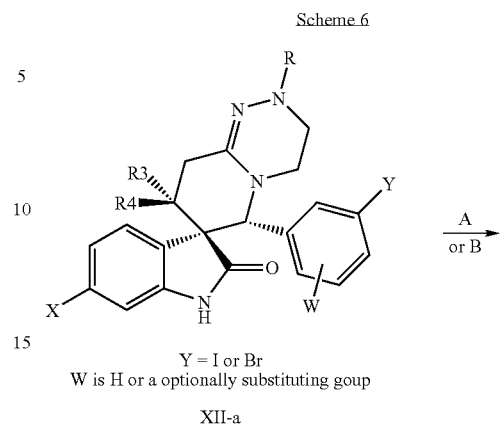

Y = I or Br
W is H or a optionally substituting goup

XII-a

R$_6$ = H, Me, CF$_3$, ethyl, isopropyl, cyclopropyl, tert-butyl

XII-b

Reagents and conditions:
A) CuI, NEt$_3$, PdCl$_2$(PPh$_3$)$_2$ (cat.), 100° C. ≡≡─R6
B) If R$_6$ = H: CuI, NEt$_3$, trimethylsilyl acetylene, PdCl$_2$(PPh$_3$)$_2$ (cat.), 100° C.; then NaOH/MeOH, rt, In a similar manner to the methods described in Scheme 5, a racemic mixture of XII and XII' in formula I can be prepared by substituting starting material VII with the racemic mixture of VII and VII'. All the compounds XII and XII', intermediates V and V', or intermediate VII and VII' were generated initially as a racemic mixture. All these racemic mixture in the reaction schemes above can also be readily separated into chiral enantiomeric pairs in a similar manner to the method in scheme 7.

Scheme 7

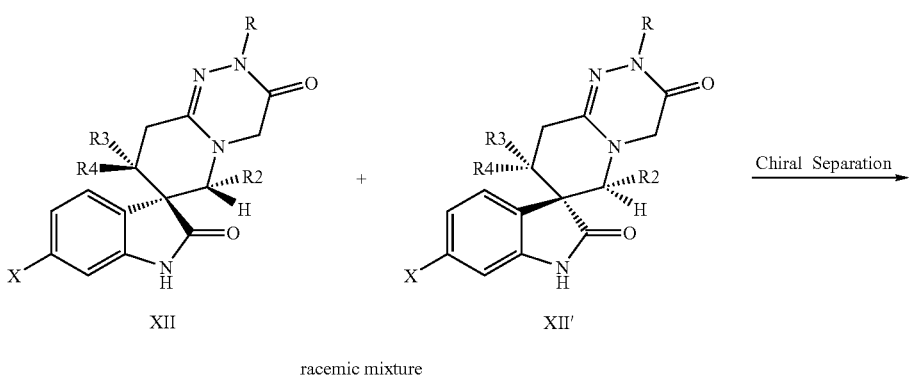

racemic mixture

-continued

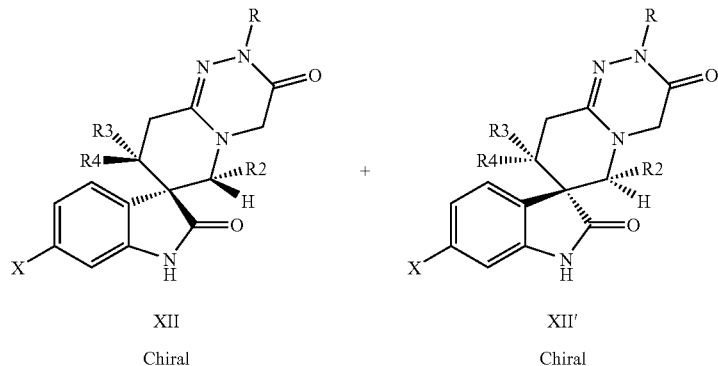

XII
Chiral

XII'
Chiral

The following examples and references are provided to aid the understanding of the present invention, the true scope of which is set forth in the appended claims.

EXAMPLE 1a

Preparation of intermediate E/Z-6-chloro-3-(3-chloro-benzylidene)-1,3-dihydro-indol-2-one

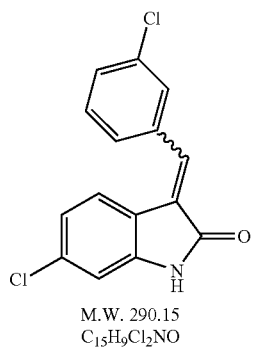

M.W. 290.15
$C_{15}H_9Cl_2NO$

To the mixture of 6-chlorooxindole (16.2 g 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 95%).

EXAMPLE 1b

Preparation of intermediate E/Z-6-chloro-3-(3-chloro-benzylidene)-1-(2-trimethylsilanyl-ethoxymethyl)-1,3-dihydro-indole-2-one

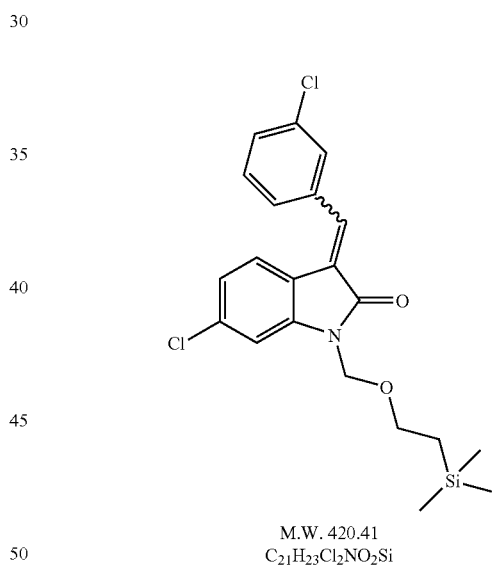

M.W. 420.41
$C_{21}H_{23}Cl_2NO_2Si$

To a solution of E/Z-6-chloro-3-(3-chloro-benzylidene)-1,3-dihydro-indol-2-one prepared in example 1a (2.3 g, 7.9 mmol) in N,N-dimethyl-formamide (20 mL) at 0° C. was added NaH (60% in mineral oil) (0.32 g, 7.9 mmol) (Aldrich), followed by the dropwise addition of 2-(trimethylsilyl) ethoxymethyl chloride (1.32 g, 7.9 mmol) in tetrahydrofuran (20 mL). The reaction mixture was stirred at 0° C. for 0.5 h, then poured into ice-water. The crude was extracted with ethyl acetate twice. The combined organic layer was dried over $Na_2SO_4$. The solvent was removed and the residue was purified by chromatography (EtOAc:hexanes=1:5) to give E/Z-6-chloro-3-(3-chloro-benzylidene)-1-(2-trimethylsilanyl-ethoxymethyl)-1,3-dihydro-indole-2-one as yellow oil (Yield 3.0 g, 90%).

EXAMPLE 1c

Preparation of intermediate 1-(5-fluoro-2-methylphenyl)-3-trimethylsilyoxy-2-aza-1,3-butadiene

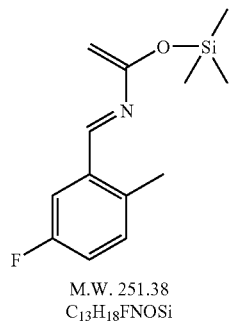

M.W. 251.38
$C_{13}H_{18}FNOSi$

To 1,1,3,3,3-hexamethyldisilazane (1.61 g, 10 mmol) (Aldrich) under nitrogen at room temperature was added n-butyllithium (2.5 M, 4 mL, 10 mmol) (Aldrich). The reaction mixture was stirred at room temperature for 10 minutes. Then dry tetrahydrofuran (30 mL) was added, followed by the addition of 5-fluoro-2-methyl-benzaldehyde (1.38 g, 10 mmol) (Platte). After the mixture was stirred at room temperature for 0.5 h, trimethylsilyl chloride (1.1 g, 10 mmol) (Aldrich) was added dropwise. Then the temperature of the mixture was lowered to 0° C. on a cooling ice bath. To this mixture was added triethylamine (1.4 g, 13.6 mmol) in one portion, followed by the dropwise addition of a solution of acetyl chloride (1 g, 13.6 mmol) in diethyl ether (50 mL). The cooling bath was removed, and the mixture was stirred at room temperature for 1 h. The mixture was quickly filtered on celite under nitrogen, and filtrate was concentrated under reduced pressure to give crude 1-(5-fluoro-2-methylphenyl)-3-trimethylsilyoxy-2-aza-1,3-butadiene as a yellow gum and used for the next step without further purification.

Similar transformation has been reported by Ghosez, L., Bayard, Ph. Nshimyumukiza, P., Gouverneur, V., Sainte, F., Beaudegnies, R., Rivers, M., Frique-Hesbain, A.-M. and Wynants, C. in *Tetrahedron* 1995, 11021-11042.

EXAMPLE 1d

Preparation of intermediate racemic (2'R, 3R, 4'S)-6-chloro-4'-(3-chlorophenyl)-2'-(5-fluoro-2-methylphenyl)-2,3-dihydro-2,6'-dioxo spiro[indole-3,3'-piperidine]-1-methoxyethyl trimethylsilane

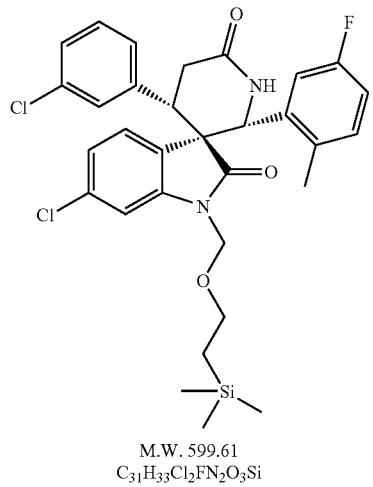

M.W. 599.61
$C_{31}H_{33}Cl_2FN_2O_3Si$

To a solution of 1-(5-fluoro-2-methylphenyl)-3-trimethylsilyoxy-2-aza-1,3-butadiene prepared in example 1c in toluene (50 mL) was added E/Z-6-chloro-3-(3-chloro-benzylidene)-1-(2-trimethylsilanyl-ethoxymethyl)-1,3-dihydroindole-2-one prepared in example 1b (3.0 g, 7.14 mmol). The reaction mixture was stirred under nitrogen in a sealed tube at 1480G for 40 min. After the solution was cooled to room temperature, methanol (50 mL) was added, and then the mixture was concentrated. The residue was purified by chromatography (EtOAc:Hexane=2:1) to give racemic (2'R, 3R, 4'S)-6-chloro-4'-(3-chlorophenyl)-2'-(5-fluoro-2-methylphenyl)-2,3-dihydro-2,6'-dioxo spiro[indole-3,3'-piperidine]-1-methoxyethyl trimethylsilane as an off-white solid (Yield 2.1 g, 49%).

EXAMPLE 1e

Preparation of intermediate racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2,6'-dioxo spiro[indole-3,3'-piperidine]-1-methoxyethyl trimethylsilane

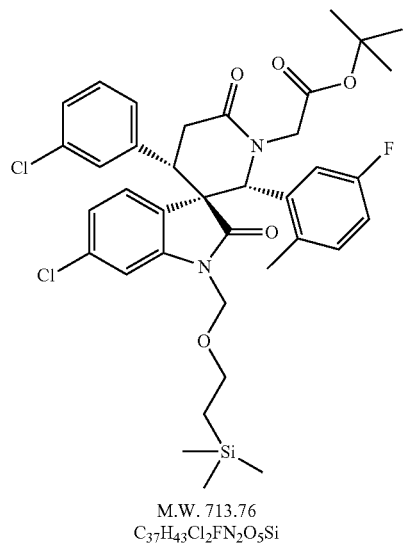

M.W. 713.76
$C_{37}H_{43}Cl_2FN_2O_5Si$

To a solution of racemic (2'R, 3R, 4'S)-6-chloro-4'-(3-chlorophenyl)-2'-(5-fluoro-2-methylphenyl)-2,3-dihydro-2,6'-dioxo spiro[indole-3,3'-piperidine]-1-methoxyethyl trimethylsilane (1.0 g, 1.67 mmol) prepared in example 1d in N,N-dimethyl-formamide (20 mL) at room temperature was added bromo-acetic acid tert-butyl ester (0.8 g, 4.1 mmol) and cesium carbonate (3.0 g, 9.20 mmol). The reaction mixture was stirred under nitrogen for 4 h, then poured into saturated aqueous $NH_4Cl$ solution. The mixture was extracted with ethyl acetate. The organic layers were combined, dried over $Na_2SO_4$ and concentrated. The residue was purified by chromatography (EtOAc:Hexanes=1:4) to give racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2,6'-dioxo spiro[indole-3,3'-piperidine]-1-methoxyethyl trimethylsilane as a white foam (Yield 0.58 g, 48.7%).

EXAMPLE 1f

Preparation of intermediate racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2-oxo-6'-thioxo spiro[indole-3,3'-piperidine]-1-methoxyethyl trimethylsilane

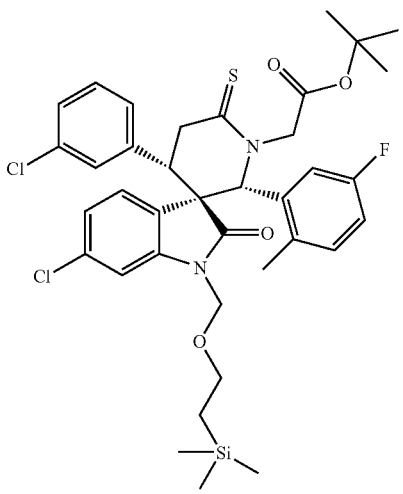

M.W. 729.82
C$_{37}$H$_{43}$Cl$_2$FN$_2$O$_4$SSi

The mixture of racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2,6'-dioxo spiro[indole-3,3'-piperidine]-1-methoxyethyl trimethylsilane (1 g, 1.4 mmol) prepared in example 1e and 2,4-bis-(4-methoxyphenyl)-1,3-dithia-2,4-diphosphetane 2,4-disulfide (1.5 g, 3.75 mmol) (Aldrich) in toluene (20 mL) was heated at 120° C. for 0.5 h. The mixture was cooled to room temperature and then concentrated. The residue was purified by chromatography (EtOAc:hexanes=1:1) to give racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2-oxo-6'-thioxo spiro[indole-3,3'-piperidine]-1-methoxyethyl trimethylsilane as a off white foam (Yield 1.0 g, 92%).

EXAMPLE 1g

Preparation of intermediate racemic (6'R, 3R, 8'S)-6-chloro-8'-(3-chlorophenyl)-6'-(5-fluoro-2-methylphenyl)-6',7',8',9'-tetrahydro-2-oxo spiro[3H-indole-3,7'-(2H-pyrido[2,1-c][1,2,4]triazin-3'-one)]-1-methoxyethyl trimethylsilane

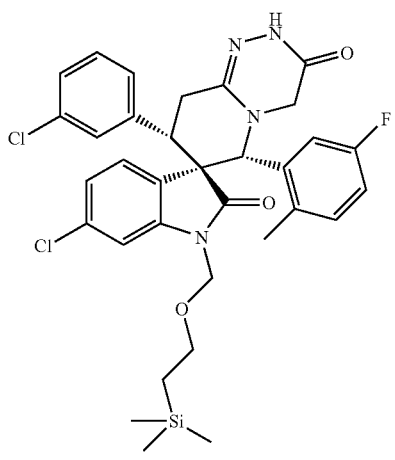

M.W. 653.66 C$_{33}$H$_{35}$Cl$_2$FN$_4$O$_3$Si

The mixture of racemic (2'R, 3R, 4'S)-6-chloro-4'-(3-chlorophenyl)-2'-(5-fluoro-2-methylphenyl)-2,3-dihydro-1'-[(tert-butoxycarbonyl)methyl]-2-oxo-6'-thioxo spiro[indole-3,3'-piperidine]-1-methoxyethyl trimethylsilane (1 g, 1.37 mmol) prepared in example 1f and hydrazine monohydrate (5 g, ~64 mmol) (Aldrich, 64-65%) in methanol (50 ml) was sealed in a tube and heated at 110° C. for 24 h. The mixture was cooled to room temperature and then concentrated. The residue was purified by chromatography (EtOAc) to give racemic (6'R, 3R, 8'S)-6-chloro-8'-(3-chlorophenyl)-6'-(5-fluoro-2-methylphenyl)-6',7',8',9'-tetrahydro-2-oxo spiro[3H-indole-3,7'-(2H-pyrido[2,1-c][1,2,4]triazin-3'-one)]-1-methoxyethyl trimethylsilane as off white solid (Yield 0.3 g, 34%).

EXAMPLE 1h

Preparation of intermediate racemic (6'R, 3R, 8'S)-6-chloro-8'-(3-chlorophenyl)-6'-(5-fluoro-2-methylphenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane

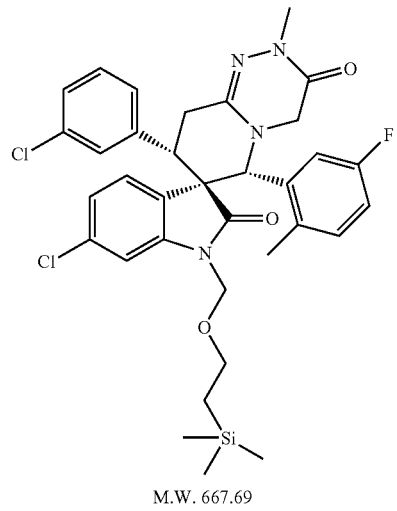

M.W. 667.69
C$_{34}$H$_{37}$Cl$_2$FN$_4$O$_3$Si

To a solution of racemic racemic (6'R, 3R, 8'S)-6-8'-(3-chlorophenyl)-6'-(5-fluoro-2-methylphenyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.15 g, 0.23 mmol) prepared in example 1g in N,N-dimethyl-formamide (20 mL) at 0° C. was added LiH (0.2 g, 25 mmol) (Aldrich), followed by the addition of iodomethane (0.39 g, 2.74 mmol). The reaction mixture was warmed up to room temperature and stirred at room temperature for 2 h. The mixture was diluted with ethyl acetate, and then washed with saturated NH$_4$Cl solution. The aqueous layer was extracted with ethyl acetate and the combined organic layer was dried over MgSO$_4$. The solvent was removed and the residue was purified by chromatography (EtOAc) to give racemic (6'R, 3R, 8'S)-6-chloro-8'-(3-chlorophenyl)-6'-(5-fluoro-2-methylphenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane (Yield 0.15 g, 98%).

EXAMPLE 1i

Preparation of racemic (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione

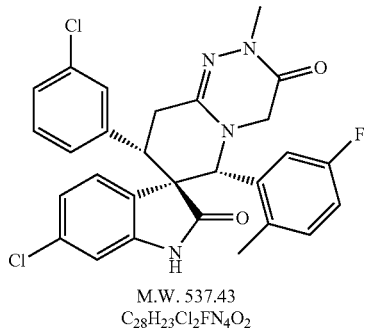

M.W. 537.43
$C_{28}H_{23}Cl_2FN_4O_2$

To a solution of racemic (6'R, 3R, 8'S)-6-chloro-8'-(3-chlorophenyl)-6'-(5-fluoro-2-methylphenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane (0.15 g, 0.22 mmol) prepared in example 1h in dichloromethane (20 mL) was added trifluoroacetic acid (10 mL). The reaction mixture was stirred at room temperature for 3 h. The reaction mixture was concentrated. The residue was neutralized with saturated NaHCO$_3$ aqueous solution, then extracted with ethyl acetate. The organic layer was separated, dried over MgSO$_4$ and concentrated.

To the residue was added methanol (20 mL) and N,N'-diisopropylethylamine (1 mL, 6.6 mmol). The reaction mixture was heated at 100° C. for 1 h, then cooled to room temperature, concentrated. The residue was partitioned between ethyl acetate and water. The organic layer was separated, and concentrated. The residue was purified by chromatography (EtOAc:NEt$_3$=100:0.1) to give racemic (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione as a white solid (Yield 85 mg, 72%).

HRMS (ES$^+$) m/z Calcd for $C_{28}H_{23}Cl_2FN_4O_2$+H [(M+H)$^+$]: 537.1255. Found: 537.1255.

EXAMPLE 1j

Preparation of Chiral (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione

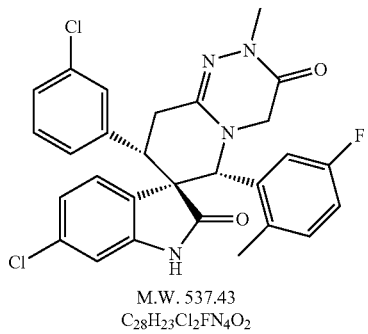

M.W. 537.43
$C_{28}H_{23}Cl_2FN_4O_2$

Separation of the two enantiomers from racemic (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione (80 mg) prepared in example 1i was conducted by chiral SFC to provide chiral (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione as a white solid (34 mg, 42%) (RO5170566-000) and chiral (6'S, 3S, 8'R)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione as a white solid (33 mg, 41%) (RO5170579-000).

EXAMPLE 2

Preparation of racemic (6'R, 3R, 8'S)-6-chloro-8'-(3-chlorophenyl)-6'-(5-fluoro-2-methylphenyl)-6',7',8',9'-tetrahydro spiro[3H-indole-3,7'-(2H-pyrido[2,1-c][1,2,4]triazine)]-2,3'(1H)-dione

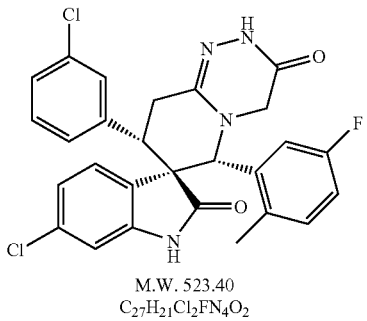

M.W. 523.40
$C_{27}H_{21}Cl_2FN_4O_2$

In a manner similar to the method described in example 1i, racemic (6'R, 3R,8'S)-6-chloro-8'-(3-chlorophenyl)-6'-(5-fluoro-2-methylphenyl)-6',7',8',9'-tetrahydro-2-oxo spiro[3H-indole-3,7'-(2H-pyrido[2,1-c][1,2,4]triazin-3'-one)]-1-methoxyethyl trimethylsilane prepared in example 1g (65 mg, 0.1 mmol) was reacted with trifluoroacetic acid (10 mL) and then N,N'-diisopropylethylamine (1 mL) to give racemic (6'R, 3R, 8'S)-6-chloro-8'-(3-chlorophenyl)-6'-(8-fluoro-2-methylphenyl)-6',7',8',9'-tetrahydro spiro[3H-indole-3,7'-(2H-pyrido[2,1-c][1,2,4]triazine)]-2,3'(1H)-dione as a white solid (25 mg, 47%).

HRMS (ES$^+$) m/z Calcd for $C_{27}H_{21}Cl_2FN_4O_2$+H [(M+H)$^+$]: 523.1099. Found: 523.1099.

EXAMPLE 3a

Preparation of intermediate 1-(1-methylene-propyl)-3-trimethylsilyoxy-2-aza-1,3-butadiene

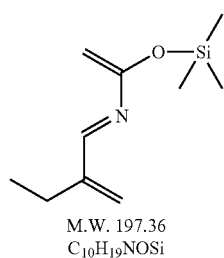

M.W. 197.36
C$_{10}$H$_{19}$NOSi

In a manner similar to the method described in example 1c, ethylacrolein (2.1 g, 22 mmol) (TCI-US) was used as the starting material in place of 5-fluoro-2-methyl-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.9 g, 27 mmol) and acetyl chloride (2 g, 27 mmol) to give 1-(1-methylene-propyl)-3-trimethylsilyoxy-2-aza-1,3-butadiene and used for the next step without further purification.

EXAMPLE 3b

Preparation of intermediate racemic (2'R, 3R, 4'S)-6-chloro-4'-(3-chlorophenyl)-2'-(1-methylene-propyl)-2,3-dihydro-2,6'-dioxo-spiro[indole-3,3'-piperidine]-1-methoxyethyl trimethylsilane

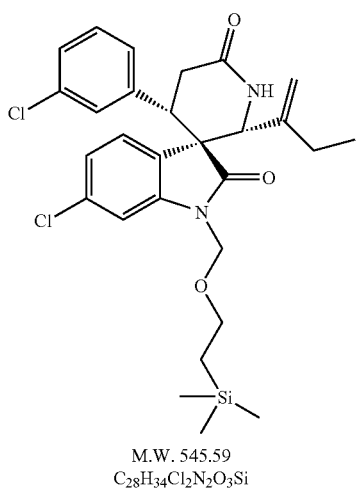

M.W. 545.59
C$_{28}$H$_{34}$Cl$_2$N$_2$O$_3$Si

In a manner similar to the method described in example 1d, E/Z-6-chloro-3-(3-chloro-benzylidene)-1-(2-trimethylsilanyl-ethoxymethyl)-1,3-dihydro-indole-2-one (3 g, 7.1 mmol) prepared in example 1b was reacted with 1-(1-methylene-propyl)-3-trimethylsilyoxy-2-aza-1,3-butadiene (19 g, 96 mmol) prepared in example 3a in toluene (200 mL) to give racemic (2'R, 3R, 4'S)-6-4'-(3-chloro-phenyl)-2'-(1-methylene-propyl)-2,3-dihydro-2,6'-dioxo spiro[indole-3,3'-piperidine]-1-methoxyethyl trimethylsilane as a white foam (Yield 3.5 g, 90%).

EXAMPLE 3c

Preparation of intermediate racemic (2'R, 3R, 4'S)-6-chloro-4'-(3-chlorophenyl)-2'-(1-methylene-propyl)-2,3-dihydro-1'-[(tert-butoxycarbonyl)methyl]-2,6'-dioxo spiro[indole-3,3'-piperidine]-1-methoxyethyl trimethylsilane

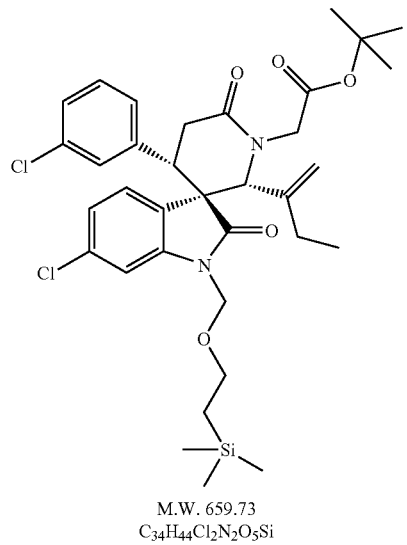

M.W. 659.73
C$_{34}$H$_{44}$Cl$_2$N$_2$O$_5$Si

In a manner similar to the method described in example 1e, racemic (2'R, 3R, 4'S)-6-chloro-4'-(3-chloro-phenyl)-2'-(1-methylene-propyl)-2,3-dihydro-2,6'-dioxo spiro[indole-3,3'-piperidine]-1-methoxyethyl trimethylsilane (7 g, 12.8 mmol) prepared in example 3b was reacted with bromo-acetic acid tert-butyl ester (10 g, 51 mmol) and cesium carbonate (11 g, 34 mmol) in N,N-dimethyl-formamide (50 mL) at room temperature to give racemic (2R, 3R, 4'S)-chloro-4'-(3-chlorophenyl)-2'-(1-methylene-propyl)-2,3-dihydro-1'-[(tert-butoxycarbonyl)methyl]-2,6'-dioxo spiro[indole-3,3'-piperidine]-1-methoxyethyl trimethylsilane as a yellow foam (Yield 5.7 g, 67%).

EXAMPLE 3d

Preparation of intermediate racemic (2'R, 3R, 4'S)-6-chloro-4'-(3-chlorophenyl)-2'-(1-methylene-propyl)-2,3-dihydro-1'-[(tert-butoxycarbonyl)methyl]-2-oxo-6'-thioxo spiro[indole-3,3'-piperidine]-1-methoxyethyl trimethylsilane

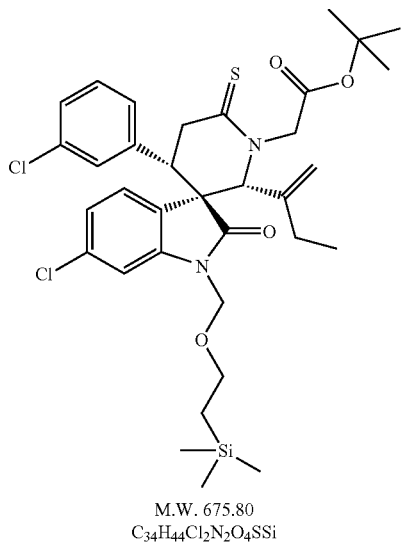

M.W. 675.80
C$_{34}$H$_{44}$Cl$_2$N$_2$O$_4$SSi

In a manner similar to the method described in example 1f, racemic (2'R, 3R,4'S)-6-chloro-4'-(3-chlorophenyl)-2'-(1-methylene-propyl)-2,3-dihydro-1'-[(tert-butoxycarbonyl)methyl]-2,6'-dioxo spiro[indole-3,3'-piperidine]-1-methoxyethyl trimethylsilane (4.7 g, 7.1 mmol) prepared in example 3c was reacted with 2,4-bis-(4-methoxyphenyl)-1,3-dithia-2,4-diphosphetane 2,4-disulfide (6 g, 15 mmol) (Aldrich) in toluene (100 mL) at 120° C. to give racemic (2'R, 3R, 4'S)-6-chloro-4'-(3-chlorophenyl)-2'-(1-methylene-propyl)-2,3-dihydro-1'-[(tert-butoxycarbonyl)methyl]-2-oxo-6'-thioxo spiro[indole-3,3'-piperidine]-1-methoxyethyl trimethylsilane as a white foam (Yield 3.5 g, 73%).

EXAMPLE 3e

Preparation of intermediate racemic (6'R, 3R, 8'S)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsiane

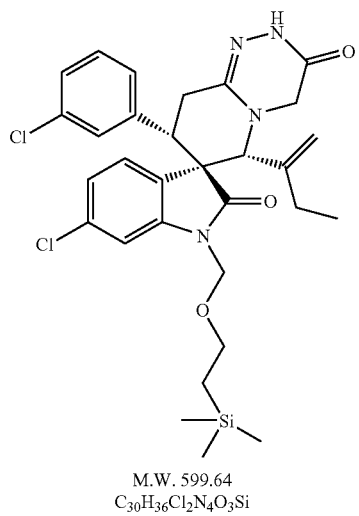

M.W. 599.64
C$_{30}$H$_{36}$Cl$_2$N$_4$O$_3$Si

In a manner similar to the method described in example 1g, racemic (2'R, 3R, 4'S)-6-chloro-4'-(3-chlorophenyl)-2'-(1-methylene-propyl)-2,3-dihydro-1'-[(tert-butoxycarbonyl)methyl]-2-oxo-6'-thioxo spiro[indole-3,3'-piperidine]-1-methoxyethyl trimethylsilane (1.9 g, 2.8 mmol) prepared in example 3d was reacted with hydrazine monohydrate (4 g, ~51 mmol) (Aldrich, 64-65%) in methanol (50 ml) in a sealed tube at 120° C. to give racemic (6'R, 3R, 8'S)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1 methoxyethyl trimethylsilane as a white foam (Yield 1.2 g, 71%).

EXAMPLE 3f

Preparation of intermediate racemic (6'R, 3R, 8'S)-6-chloro-8'-(3-chlorophenyl)-6'-(1-methylene-propyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane

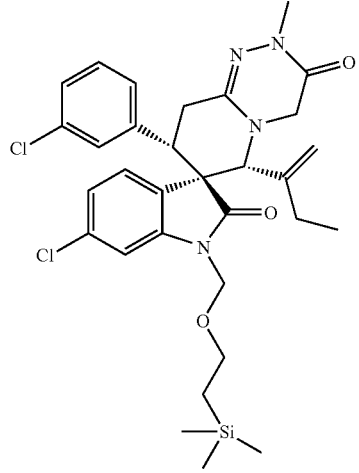

M.W. 613.67
C$_{31}$H$_{38}$Cl$_2$N$_4$O$_3$Si

In a manner similar to the method described in example h, racemic (6'R, 3R, 8'S)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.11 g, 0.18 mmol) prepared in example 3e was reacted with LiH (0.2 g, 25 mmol) (Aldrich) and iodomethane (3 g, 21 mmol) in N,N-dimethyl-formamide (20 mL) to give racemic (6'R, 3R, 8'S)-6-chloro-8'-(3-chlorophenyl)-6'-(1-methylene-propyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane as a white foam (Yield 0.11 g, 99%).

EXAMPLE 3g

Preparation of racemic (6'R, 3R, 8'S)-6-chloro-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione

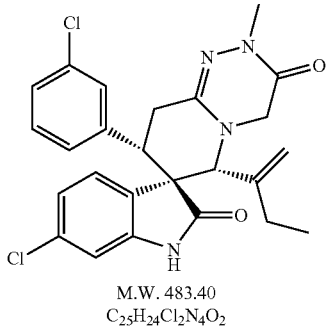

M.W. 483.40
$C_{25}H_{24}Cl_2N_4O_2$

In a manner similar to the method described in example 1i, (6'R, 3R, 8S)-6-chloro-8'-(3-chlorophenyl)-6'-(1-methylene-propyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane (0.11 g, 0.18 mmol) prepared in example 3f was reacted with trifluoroacetic acid, followed by reaction with N,N'-diisopropylethylamine in methanol to give racemic (6'R, 3R, 8'S)-6-chloro-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione as a white solid (Yield 61 mg, 70%).

HRMS (ES$^+$) m/z Calcd for $C_{25}H_{24}Cl_2N_4O_2$+H [(M+H)$^+$]: 483.1349. Found: 483,1348.

EXAMPLE 3h

Preparation of Chiral (6'R, 3R, 8'S)-6-chloro-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione

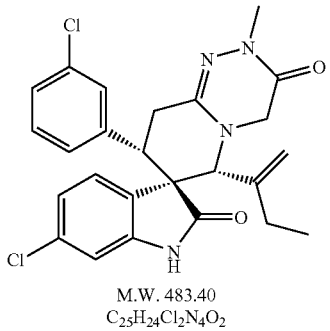

M.W. 483.40
$C_{25}H_{24}Cl_2N_4O_2$

Separation of the two enantiomers from racemic (6'R, 3R, 8'S)-6-chloro-8'-(3-chlorophenyl)-6'-(1-methyl)-2'-methyl-6',7',8',9'-tetrahydro spiro[3H-indole-3,7'-(2H-pyrido[2,1-c][1,2,4]triazine)]-2,3'(1H)-dione (58 mg) prepared in example 3g was conducted by chiral SFC to provide chiral (6'R, 3R, 8'S)-6-chloro-8S-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione as a white solid (19 mg, 33%) (RO5174040-000) and chiral (6'S, 3S, 8'R)-6-chloro-8'-(3-chlorophenyl)-6'-(1-methylene-propyl)-2'-methyl-6',7',8',9'-tetrahydro spiro[3H-indole-3,7'-(2H-pyrido[2,1-c][1,2,4]triazine)]-2,3'(1H)-dione as a white solid (23 mg, 40%) (RO5174041-000).

EXAMPLE 4a

Preparation of racemic (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione

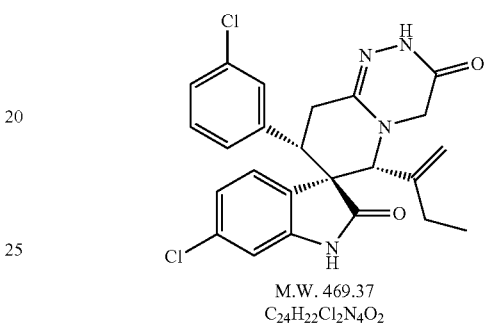

M.W. 469.37
$C_{24}H_{22}Cl_2N_4O_2$

In a manner similar to the method described in example 1i, racemic (6'R, 3R,8'S)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.11 g, 0.18 mmol) prepared in example 3e (100 mg, 0.17 mmol) was reacted with trifluoroacetic acid and then N,N'-diisopropylethylamine in methanol to give racemic (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (43 mg, 55%).

HRMS (ES$^+$) m/z Calcd for $C_{24}H_{22}Cl_2N_4O_2$+H [(M+H)$^+$]-469.1193. Found: 469.1189.

EXAMPLE 4b

Preparation of Chiral (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione

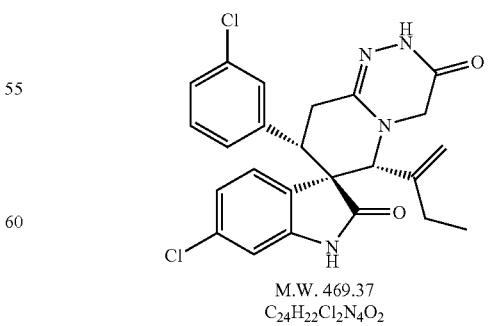

M.W. 469.37
$C_{24}H_{22}Cl_2N_4O_2$

Separation of the two enantiomers from racemic (6'R, 3R, 8'S)-6-chloro-8'-(3-chlorophenyl)-6'-(1-methylene-propyl)-

6',7',8',9'-tetrahydro spiro[3H-indole-3,7'-(2H-pyrido[2,1-c][1,2,4]triazine)]-2,3'(1H)-dione (43 mg) prepared in example 4a was conducted by chiral SFC to provide chiral (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (21 mg, 50%) (RO5186112-000) and chiral (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (18 mg, 42%).

EXAMPLE 5a

Preparation of intermediate racemic (6'R, 3R, 8'S)-6-chloro-8'-(3-chlorophenyl)-2'-(3-dimethylaminopropyl)-6'-(1-methylene-propyl)-6',7',8',9'-tetrahydro-2-oxo spiro[3H-indole-3,7'-(2H-pyrido[2,1-c][1,2,4]triazin-3'-one)]-1 methoxyethyl trimethylsilane

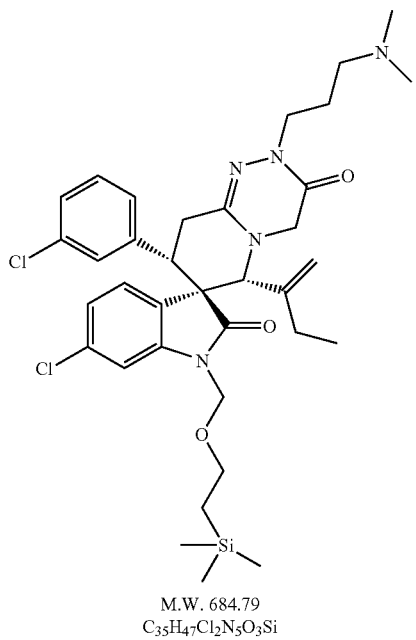

M.W. 684.79
$C_{35}H_{47}Cl_2N_5O_3Si$

In a manner similar to the method described in example 1h, racemic (6'R, 3R,8'S)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.12 g, 0.20 mmol) prepared in example 3e was reacted with LiH (0.3 g, 38 mmol) (Aldrich) and 3-dimethylaminopropyl chloride hydrochloride (0.8 g, 5 mmol) (Aldrich) in N,N-dimethyl-formamide (10 mL) at 100° C. for 3 h to give racemic (6'R, 3R 8'S)-6-chloro-8'-(3-chlorophenyl)-2'-(3-dimethylaminopropyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane as a white foam (Yield 0.12 g, 88%).

EXAMPLE 5b

Preparation of racemic (6'R, 3R, 8'S)-6-chloro-8'-(3-chlorophenyl)-2'-(3-dimethylaminopropyl)-6'-(1-methylene-propyl)-6',7',8',9'-tetrahydro spiro[3H-indole-3,7'-(2H-pyrido[2,1-c][1,2,4]triazine)]-2,3'(1H)-dione

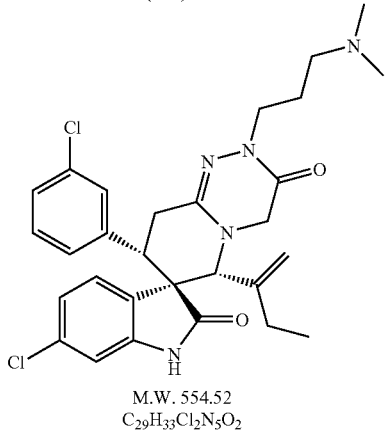

M.W. 554.52
$C_{29}H_{33}Cl_2N_5O_2$

In a manner similar to the method described in example 1i, racemic (6'R, 3R, 8'S)-6-8'-(3-chlorophenyl)-2'-(3-dimethylaminopropyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.12 g, 0.18 mmol) prepared in example 5a was reacted with trifluoroacetic acid, followed by reaction with N,N'-diisopropylethylamine in methanol to give racemic (6'R, 3R, 8'S)-6-chloro-8'-(3-chlorophenyl)-2'-(3-dimethylaminopropyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (Yield 57 mg, 57%).

HRMS (ES+) m/z Calcd for $C_{29}H_{33}Cl_2N_5O_2+H$ [(M+H)+]: 554.2084. Found: 554.2083.

EXAMPLE 6a

Preparation of intermediate racemic (6'R, 3R, 8'S)-6-chloro-8'-(3-chlorophenyl)-2'-(2-methoxyethyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane

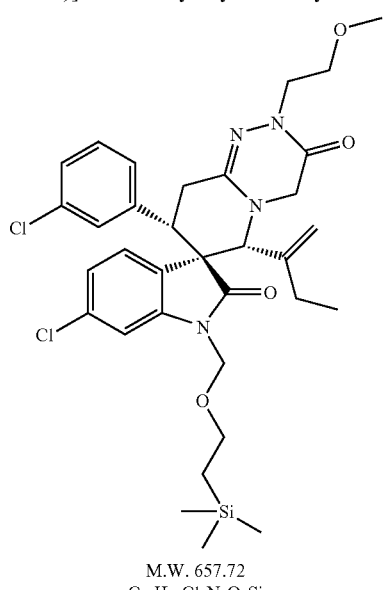

M.W. 657.72
$C_{33}H_{42}Cl_2N_4O_4Si$

In a manner similar to the method described in example 1h, racemic (6'R, 3R, 8' S)-6-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.1 g, 0.17 mmol) prepared in example 3e was reacted with LiH (0.3 g, 38 mmol) (Aldrich) and 2-bromoethyl methyl ether (5 g, 36 mmol) (Aldrich) in N,N-dimethyl-formamide (10 mL) at room temperature for 10 h to give racemic (6'R, 3R, 8'S)-6-chloro-8'-(3-chlorophenyl)-2'-(2-methoxyethyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane as a white foam (Yield 0.1 g, 89%).

EXAMPLE 6b

Preparation of racemic (6'R, 3R, 8'S)-6-chloro-8'-(3-chlorophenyl)-2'-(2-methoxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione

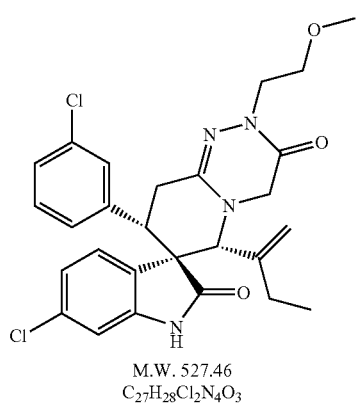

M.W. 527.46
C₂₇H₂₈Cl₂N₄O₃

In a manner similar to the method described in example 1i, racemic (6'R, 3R, 8'S)-6-chloro-8'-(3-chlorophenyl)-2'-(3-dimethylaminopropyl)-6'-(1-methylene-propyl)-6',7',8',9'-tetrahydro-2-oxo spiro[3H-indole-3,7'-(2H-pyrido[2,1-c][1,24]triazin-3'-one)]-1-methoxyethyl trimethylsilane (0.1 g, 0.18 mmol) prepared in example 6a was reacted with trifluoroacetic acid, followed by reaction with N,N'-diisopropylethylamine in methanol to give racemic (6'R, 3R, 8'S)-6-chloro-8'-(3-chlorophenyl)-2'-(2-methoxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (Yield 38 mg, 47%).

HRMS (ES⁺) m/z Calcd for C₂₇H₂₈Cl₂N₄O₃+H [(M+H)⁺]: 527.1611. Found: 527.1610.

EXAMPLE 7a

Preparation of intermediate racemic (6'R, 3R, 8'S)-2'-(2-acetoxyethyl)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane

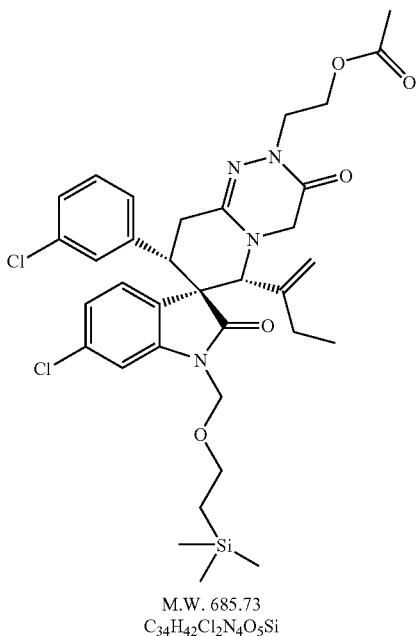

M.W. 685.73
C₃₄H₄₂Cl₂N₄O₅Si

In a manner similar to the method described in example 1h, racemic (6'R, 3R, 8'S)-6-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.5 g, 0.83 mmol) prepared in example 3e was reacted with LiH (0.2 g, 25 mmol) (Aldrich) and 2-bromoethyl acetate (1.2 g, 7 mmol) (Aldrich) in N,N-dimethyl-formamide (30 mL) at room temperature for 72 h to give racemic (6'R, 3R, 8'S)-2'-(2-acetoxyethyl)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane as a white foam (Yield 0.51 g, 90%).

EXAMPLE 7b

Preparation of racemic (6'R, 3R, 8'S)-2'-(2-acetoxy-ethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione

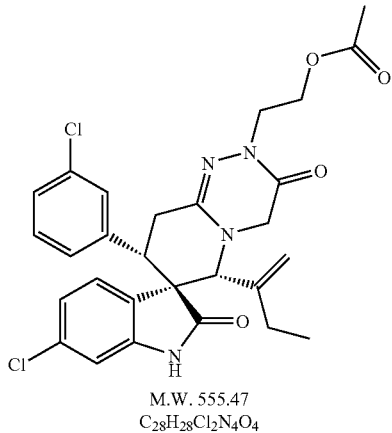

M.W. 555.47
$C_{28}H_{28}Cl_2N_4O_4$

In a manner similar to the method described in example 1i, racemic (6'R, 3R, 8'S)-2'-(2-acetoxyethyl)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.51 g, 0.74 mmol) prepared in example 6a was reacted with trifluoroacetic acid in dichloromethane at room temperature for 5 h, followed by reaction with N,N'-diisopropylethylamine in methanol at 100° C. for 0.5 h to give racemic (6'R, 3R, 8'S)-2'-(2-acetoxyethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (Yield 0.35 g, 85%).

HRMS (ES$^+$) m/z Calcd for $C_{28}H_{28}Cl_2N_4O_4{}^+H$ [(M+H)$^+$]- 555.1561 Found: 555.1558.

EXAMPLE 8a

Preparation of racemic (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione

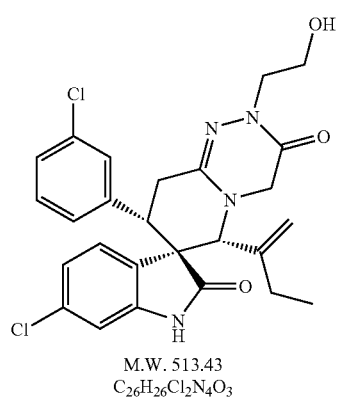

M.W. 513.43
$C_{26}H_{26}Cl_2N_4O_3$

To a solution of racemic (6'R, 3R, 8'S)-2'-(2-acetoxyethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione (0.3 g, 0.54 mmol) prepared in example 7b in tetrahydrofuran (25 mL) and methanol (15 mL) was added sodium hydroxide aqueous solution (1N, 10 mL). the reaction mixture was stirred at room temperature for 2 h, then neutralized to "pH" 7 by aqueous HCl. The mixture was then extracted with ethyl acetate. The organic layer was separated, died over MgSO$_4$, concentrated, and dried in vacuo to give racemic racemic (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (0.22 g, 79%)

HRMS (ES$^+$) m/z Calcd for $C_{26}H_{26}Cl_2N_4O_3$+H [(M+H)$^+$]: 513.1455. Found: 513.1452.

EXAMPLE 8b

Preparation of Chiral (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione

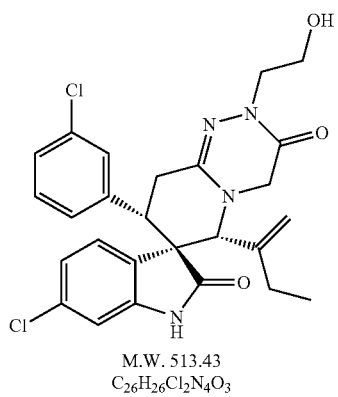

M.W. 513.43
$C_{26}H_{26}Cl_2N_4O_3$

Separation of the two enantiomers from racemic (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione (220 mg) prepared in example 8a was conducted by chiral SFC to provide chiral (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (90 mg, 41%) (RO5184375-000) and chiral (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (98 mg, 45%) (RO5174422-000).

EXAMPLE 9a

Preparation of intermediate racemic (6'R, 3R, 8'S)-2'-(2-acetylaminoethyl)-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane

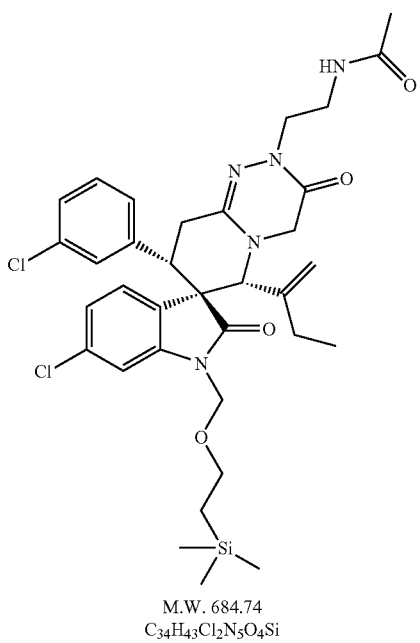

M.W. 684.74
$C_{34}H_{43}Cl_2N_5O_4Si$

In a manner similar to the method described in example 1h, racemic (6'R, 3R, 8'S)-6-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (50 mg, 0.083 mmol) prepared in example 3e was reacted with LiH (0.2 g, 25 mmol) (Aldrich), NaI (0.2 g), and N-(2-chloroethyl)acetamide (1 g, 8 mmol) (Alfa) in N,N-dimethyl-formamide (30 mL) at room temperature for 72 h to give racemic (6'R, 3R, 8'S)-2'-(2-acetylaminoethyl)-6-chloro-8'-(3-chlorophenyl)-6'-(1-methylene-propyl)-6',7',8', 9'-tetrahydro-2-oxo spiro[3H-indole-3,7'-(2H-pyrido[2,1-c][1,2,4]triazin-3'-one)]-1-methoxyethyl trimethylsilane as a white foam (Yield 32 mg, 56%).

EXAMPLE 9b

Preparation of racemic (6'R, 3R, 8'S)-2'-(2-acetylaminoethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1)-dione

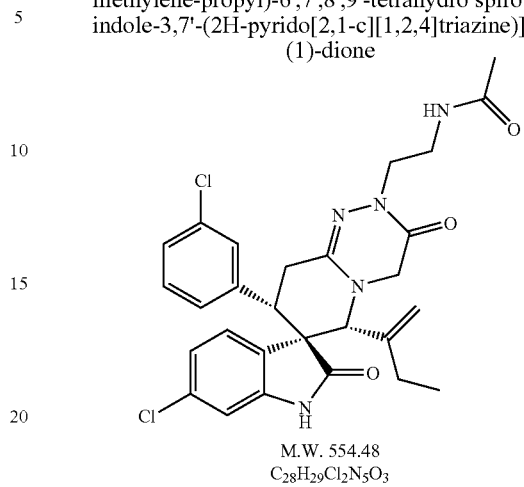

M.W. 554.48
$C_{28}H_{29}Cl_2N_5O_3$

In a manner similar to the method described in example 1i, racemic (6'R, 3R,8'S)-2'-(2-acetylaminoethyl)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (32 mg, 0.047 mmol) prepared in example 9a was reacted with trifluoroacetic acid in dichloromethane at room temperature for 1 h to give racemic (6'R, 3R, 8'S)-2'-(2-acetylaminoethyl)-6-chloro-8'-(3-chlorophenyl)-6'-(1-methylene-propyl)-6',7',8', 9'-tetrahydro spiro[3H-indole-3,7'-(2H-pyrido[2,1-c][1, 2,4] triazine)]-2,3'(1H)-dione as a white solid (Yield 15 mg, 57%).

HRMS (ES$^+$) m/z Calcd for $C_{28}H_{29}Cl_2N_5O_3$+H [(M+H)$^+$]: 554.1720. Found: 554.1716.

EXAMPLE 10a

Preparation of intermediate racemic (6'R, 3R, 8'S)-2'-(2-tert-butoxycarbonyl-methyl)-6-chloro-8'-(3-chlorophenyl)-6'-(1-methylene-propyl)-6',7',8',9'-tetrahydro-2-oxo spiro[3H-indole-3,7'-(2H-pyrido[2, 1-c][1,2,4]triazin-3'-one)]-1-methoxyethyl trimethylsilane

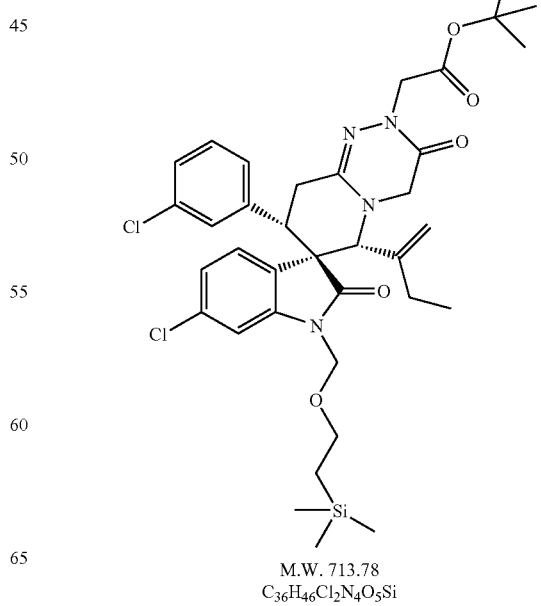

M.W. 713.78
$C_{36}H_{46}Cl_2N_4O_5Si$

To a solution of racemic (6'R, 3R, 8'S)-6-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.75 g, 1.25 mmol) prepared in example 3e in N,N-dimethyl-formamide (50 mL) at room temperature was added bromo-acetic acid tert-butyl ester (3 g, 15 mmol) and cesium carbonate (19 g 3.1 mmol). The reaction mixture was stirred under nitrogen for 5 h, then poured into saturated aqueous NH$_4$Cl solution. The mixture was extracted with ethyl acetate. The organic layers were combined, dried over Na$_2$SO$_4$ and concentrated. The residue was purified by chromatography (EtOAc:Hexanes-1:2) to give racemic (6'R, 3R, 8'S)-2'-(2-tert-butoxycarbonyl-methyl)-6-chloro-8'-(3-chlorophenyl)-6'-(1-methylene-propyl)-6',778',9'-tetrahydro-2-oxo spiro[3H-indole-3,7'-(2H-pyrido[2,1-c][1,2,4]triazin-3'-one)]-1-methoxyethyl trimethylsilane as a white solid (Yield 0.7 g, 78%).

EXAMPLE 10b

Preparation of racemic (6'R, 3R, 8'S)-6-8'-(3-chlorophenyl)-2'-(2-hydroxycarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-dione

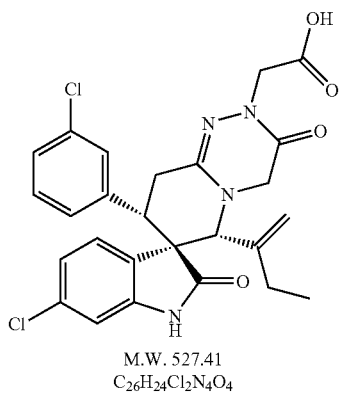

M.W. 527.41
$C_{26}H_{24}Cl_2N_4O_4$

In a manner similar to the method described in example 1i, racemic (6'R, 3R, 8'S)-2'-(2-tert-butoxycarbonyl-methyl)-6-chloro-8'-(3-chlorophenyl)-6'-(1-methylene-propyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.59 g, 0.83 mmol) prepared in example 10a was reacted with trifluoroacetic acid (10 mL) in dichloromethane (20 mL) at room temperature for 18 h, followed by reaction with N,N'-diisopropylethylamine (1 mL) in methanol (10 mL) at 100° C. for 1 h to give racemic (6R, 3R, 8'S)-chloro-8'-(3-chlorophenyl)-2'-(2-hydroxycarbonyl-methyl)-6'-(1-methylene-propyl)-6',7',8'9'-tetrahydro spiro[3H-indole-3,7'-(2H-pyrido[2,1-c][1,2,4]triazine)]-2,3'(1H)-dione as a white solid (Yield 0.3 g, 69%).

HRMS (ES$^+$) m/z Calcd for $C_{26}H_{24}Cl_2N_4O_4{}^+$H [(M+H)$^+$]: 527.1248. Found: 527.1247.

EXAMPLE 11a

Preparation of racemic (6'R, 3R, 8'S)-6-chloro-8'-(3-chlorophenyl)-2'-(2-fluorocarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-done

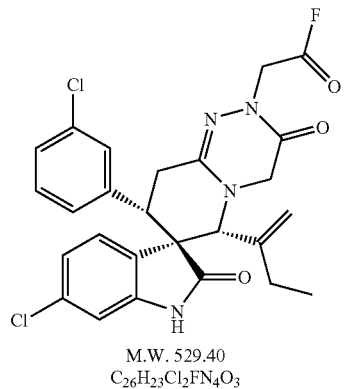

M.W. 529.40
$C_{26}H_{23}Cl_2FN_4O_3$

To the solution of racemic (6'R, 3R, 8'S)-6-chloro-8'-(3-chlorophenyl)-2'-(2-hydroxycarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-dione (1 g, 1.9 mmol) prepared in example 10b in dichloromethane (30 mL) at 0° C. was added cyanuric fluoride (1 g, 7.3 mmol) (Alfa) and pyridine (2 g, 25 mmol). After the mixture was stirred at 0° C. for 2 h, the mixture was partitioned between H$_2$O and dichloromethane. The organic layer was separated and the aqueous layer was extracted with dichloromethane. The organic layers were combined, dried over MgSO$_4$, concentrated to give racemic (6'R, 3R, 8'S)-6-chloro-8'-(3-chlorophenyl)-2'-(2-fluorocarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-dione as a yellow solid and used for the next step without further purification (Yield: 0.61 g, 60%).

EXAMPLE 11b

Preparation of racemic (6'R, 3R, 8'S)-6-chloro-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione

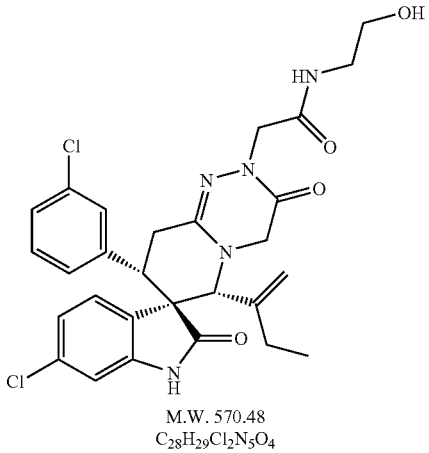

M.W. 570.48
$C_{28}H_{29}Cl_2N_5O_4$

To a solution of racemic (6'R, 3R, 8'S)-6-chloro-8'-(3-chlorophenyl)-2'-(2-fluorocarbonyl-methyl)-6'-(1-methylene-propyl)-6',7',8',9'-tetrahydro spiro[3H-indole-3,7'-(2H-pyrido[2,1-c][1,2,4]triazine)]-2,3'(II)-dione (0.2 g, 0.57 mmol) prepared in 11a in tetrahydrofuran (30 mL) in a sealed tube was added 2-aminoethanol (0.3 g, 4.9 mmol) (Aldrich), N-methylmorpholine (0.3 g, 3 mmol) and 4-dimethylaminopyridine (7 mg, 0.075 mmol). After the mixture was heated under microwave irridiation at 100° C. for 30 min. the mixture was diluted with ethyl acetate, washed with $H_2O$. The organic layer was separated, dried over $Na_2SO_4$ and concentrated. The residue was purified by chromatography (MeOH: EtOAc=1:8) to give racemic (6'R, 3R, 8'S)-6-chloro-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (Yield: 92 mg, 28%).

HRMS (ES$^+$) m/z Calcd for $C_{28}H_{29}Cl_2N_5O_4{}^+H$ [(M+H)$^+$]: 570.1670. Found: 570.1671.

EXAMPLE 11c

Preparation of Chiral (6'R, 3R, 8'S)-6-chloro-8'-(3-chlorophenyl)-2'-[(2-hydroxyethylamino)carbonyl-methyl]-6'-(1-methylene-propyl)-6',7',8',9-tetrahydro spiro[3H-indole-3,7'-(2H-pyrido[2,1-c][1,2,4]triazine)]-2,3'(1H)-dione

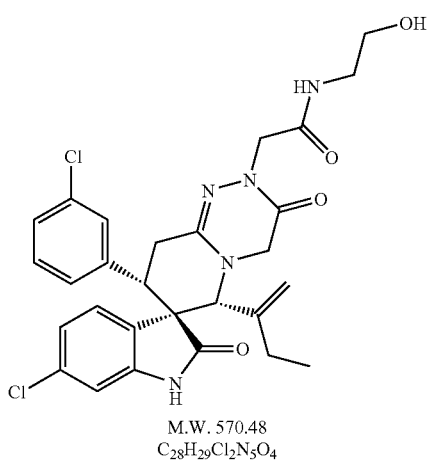

M.W. 570.48
$C_{28}H_{29}Cl_2N_5O_4$

Separation of the two enantiomers from racemic (6'R, 3R, 8'S)-6-chloro-8'-(3-chlorophenyl)-2'-[(2-hydroxyethylamino)carbonyl-methyl]-6'-(1-methylene-propyl)-6',7',8', 9'-tetrahydro spiro[3H-indole-3,7'-(2H-pyrido[2,1-c][1,2,4]triazine)]-2,3'(1H)-dione (80 mg) prepared in example 11b was conducted by chiral SFC to provide chiral (6'R, 3R, 8'S)-6-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (28 mg, 35%) (RO5185374-000) and chiral (6'S,3S,8'R)-6-chloro-8'-(3-chlorophenyl)-2'-[(2-hydroxyethylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (30 mg, 38%) (RO5185375-000).

EXAMPLE 12a

Preparation of racemic (6'R, 3R, 8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione

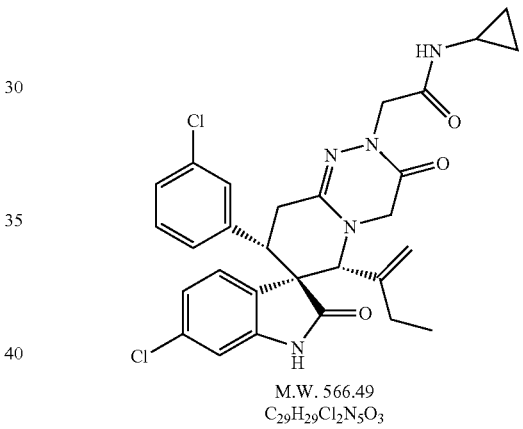

M.W. 566.49
$C_{29}H_{29}Cl_2N_5O_3$

In a manner similar to the method described in example 11b, racemic (6'R, 3R, 8'S)-6-chloro-8'-(3-chlorophenyl)-2'-(2-fluorocarbonyl-methyl)-6'-(1-methylene-propyl)-6',7',8', 9'-tetrahydro spiro[3H-indole-3,7'-(2H-pyrido[2,1-c][1,2,4] triazine)]-2,3'(1H)-dione (0.15 g, 0.28 mmol) prepared in example 11a was reacted with cyclopropylamine (Aldrich), N-methylmorpholine and 4-dimethylaminopyridine to give racemic ((6'R, 3R,8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido [2,1-c][1,2,4]triazine)]-2,3'(1H)-dione as a yellow solid (Yield 85 mg, 54%).

HRMS (ES$^+$) m/z Calcd for $C_{29}H_{29}Cl_2N_5O_3+H$ [(M+H)$^+$]: 566.1720. Found: 566.1721.

EXAMPLE 12b

Preparation of Chiral (6'R, 3R, 8;S)-6-chloro-8-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione

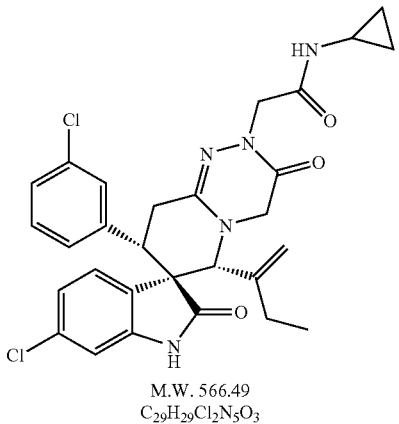

M.W. 566.49
$C_{29}H_{29}Cl_2N_5O_3$

Separation of the two enantiomers from racemic (6'R, 3R, 8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione (75 mg) prepared in example 12a was conducted by chiral SFC to provide chiral (6'R, 3R, 8'S)-6-chloro-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (27 mg, 36%) (RO5185379-000) and chiral (6'S,3S,8'R)-6-chloro-8'-(3-chlorophenyl)-2'-[(2-cyclopropylamino)carbonyl-methyl]6'-(1-methylene-propyl)-6',7',8',9'-tetrahydro spiro[3H-indole-3,7'-(2H-pyrido[2,1-c][1,2,4]triazine)]-2,3'(1H)-dione as a white solid (23 mg, 31%).

EXAMPLE 13a

Preparation of racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione

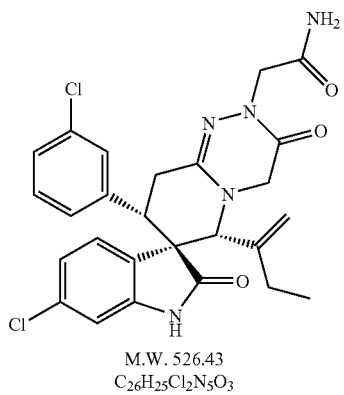

M.W. 526.43
$C_{26}H_{25}Cl_2N_5O_3$

Racemic (6'R, 3R, 8'S)-6-chloro-8'-(3-chlorophenyl)-2'-(2-fluorocarbonyl-methyl) -6'-(1-methylene-propyl)-6',7',8',9'-tetrahydro spiro[3H-indole-3,7'-(2H-pyrido[2,1-c][1,2,4]triazine)]-2,3'(1H)-dione (0.2 g, 0.38 mmol) prepared in example 11a was stirred in a methanolic ammonia solution (7N, 20 mL) at room temperature for 24 h. The reaction mixture was concentrated, and the residue was purified by chromatography (EtOAc:MeOH=9:1) to give racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (Yield 98 mg, 49%).

HRMS (ES$^+$) m/z Calcd for $C_{26}H_{25}Cl_2N_5O_3$+H [(M+H)$^+$]: 526.1407. Found: 526.1408.

EXAMPLE 13b

Preparation of racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione

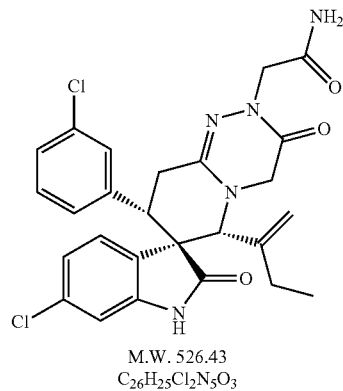

M.W. 526.43
$C_{26}H_{25}Cl_2N_5O_3$

Separation of the two enantiomers from racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione (90 mg) prepared in example 13a was conducted by chiral SFC to provide chiral (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (36 mg, 40%) (RO5185390-000) and chiral (6'S,3S,8'R)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (38 mg, 42%) (RO5185391-000).

EXAMPLE 14a

Preparation of racemic (6'R, 3R, 8'S)-6-chloro-8'-(3-chlorophenyl)-2'-[(1-methanesulfonyl-piperidin-4-yl) aminocarbonyl-methyl]-6'-(1-methylene-propyl)-6', 7',8',9'-tetrahydro spiro[3H-indole-3,7'-(2H-pyrido[2,1-c][1,2,4]triazine)]-2,3'(1H)-ione

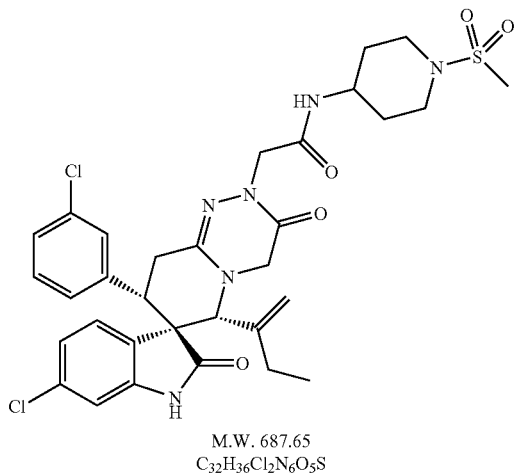

M.W. 687.65
$C_{32}H_{36}Cl_2N_6O_5S$

In a manner similar to the method described in example 11b, racemic (6'R, 3R,8'S)-6-chloro-8'-(3-chlorophenyl)-2'-(2-fluorocarbonyl-ethyl)-6'-(1-methylene-propyl)-6',7',8',9'-tetrahydro spiro[3H-indole-3,7'-(2H-pyrido[2,1-c][1,2,4]triazine)]-2,3'(1H)-dione (0.2 g, 0.38 mmol) prepared in example 11a was reacted with 1-methanesulfonyl-piperidin-4-ylamine trifluoroacetic acid salt (0.2 g), N-methylmorpholine and 4-dimethylaminopyridine to give racemic (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9-tetrahydro spiro[3H-indole-3,7'-(2H-pyrido[2,1-c][1,2,4]triazine)]-2,3'(1H)-dione as a white solid (Yield 45 mg, 17%).

HRMS (ES$^+$) m/z Calcd for $C_{32}H_{36}Cl_2N_6O_5S$+H [(M+H)$^+$]: 687.1918. Found: 687.1918.

EXAMPLE 14b

Preparation of racemic (6'R, 3R, 8'S)-6-chloro-8'-(3-chlorophenyl)-2'-[(1-methanesulfonyl-piperidin-4-yl) aminocarbonyl-methyl]-6'-(1-methylene-propyl)-6', 7',8',g-tetrahydro spiro[3H-indole-3,7'-(2H-pyrido[2,1-c][1,2,4]triazine)]-2,3'(1H)-dione

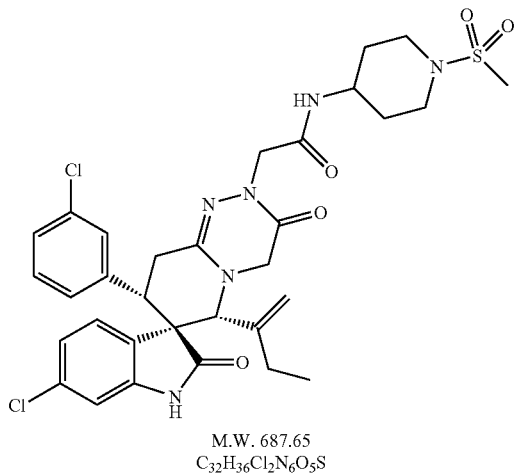

M.W. 687.65
$C_{32}H_{36}Cl_2N_6O_5S$

Separation of the two enantiomers from racemic (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido [2,1-c][1,2,4]triazine)]-2,3'(1H)-dione (40 mg) prepared in example 14a was conducted by chiral SFC to provide chiral (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9-tetrahydro spiro[3H-indole-3,7'-(2H-pyrido[2,1-c][1,2,4]triazine)]-2,3'(1H)-dione as a white solid (15 mg, 38%) (RO5185394-000) and chiral (6'S, 3S, 8'R)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido [2,1-c][1,2,4]triazine)]-2,3'(1H)-dione as a white solid (15 mg, 38%) (RO5185395-000).

EXAMPLE 15a

Preparation of intermediate 1-isopropenyl-3-trimethylsilyoxy-2-aza-1,3-butadiene

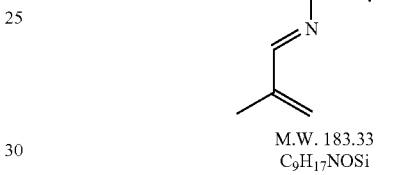

M.W. 183.33
$C_9H_{17}NOSi$

In a manner similar to the method described in example 1c, 2-methacrolein (2 g, 20 mmol) (Acros) was used as the starting material in place of 5-fluoro-2-methyl-benzaldehyde to react with 1,1,1,3,3,3-hexamethyldisilazane (3.2 g, 20 mmol), n-butyllithium (2.5 M, 8 mL, 20 mmol), trimethylsilyl chloride (2.2 g, 20 mmol), triethylamine (2.7 g, 27 mmol) and acetyl chloride (2.0 g, 27 mmol) to give 1-isopropenyl-3-trimethylsilyoxy-2-aza-1,3-butadiene and used for the next step without further purification.

EXAMPLE 15b

Preparation of intermediate racemic (2'R, 3R, 4'S)-6-4'-(3-chlorophenyl)-2'-isopropenyl-2,3-dihydro-2,6'-dioxo spiro[indole-3,3'-piperidine]-1-methoxyethyl trimethylsilane

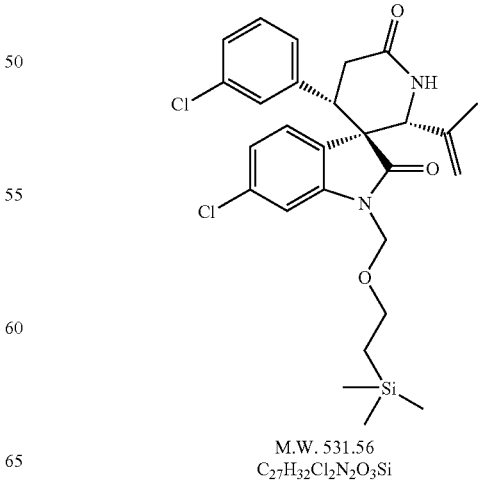

M.W. 531.56
$C_{27}H_{32}Cl_2N_2O_3Si$

In a manner similar to the method described in example 1d, E/Z-6-chloro-3-(3-chlorobenzylidene)-1-(2-trimethylsilanyl-ethoxymethyl)-1,3-dihydro-indole-2-one (8 g, 20 mmol) prepared in example 1b was reacted with 1-isopropenyl-3-trimethylsilyoxy-2-aza-1,3-butadiene (21 g, 99 mmol) prepared in example 15a in toluene (200 mL) to give racemic (2'R, 3R, 4'S)-6-chloro-4'-(3-chlorophenyl)-2'-isopropenyl-2,3-dihydro-2,6-dioxo spiro[indole-3,3'-piperidine]-1-methoxyethyl trimethylsilane as a white gum (3.5 g, 33%)

EXAMPLE 15c

Preparation of intermediate racemic (2'R, 3R, 4'S)-6-chloro-4'-3-chlorophenyl)-2'-isopropenyl-2,3-dihydro-1'-[(tert-butoxycarbonyl)methyl]-2,6'-dioxo spiro[indole-3,3'-piperidine]-1-methoxyethyl trimetane

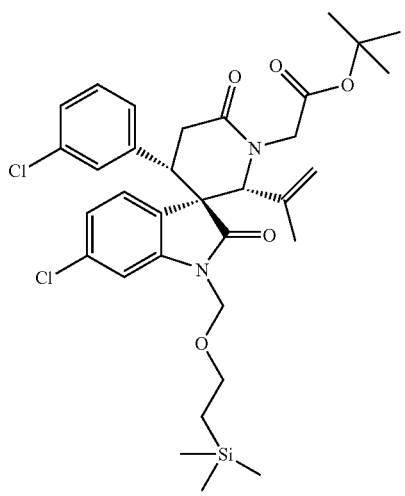

M.W. 645.71
C$_{33}$H$_{42}$Cl$_2$N$_2$O$_5$Si

In a manner similar to the method described in example 1e, racemic (2'R, 3R, 4'S)-6-4'-(3-chlorophenyl)-2'-isopropenyl-2,3-dihydro-2,6'-dioxo spiro[indole-3,3'-piperidine]-1-methoxyethyl trimethylsilane (3 g, 5.64 mmol) prepared in example 15b was reacted with bromo-acetic acid tert-butyl ester and cesium carbonate in N,N-dimethyl-formamide to give racemic (2'R, 3R, 4'S)-6-chloro-4'-(3-chlorophenyl)-2'-isopropenyl-2,3-dihydro-1'-[(tert-butoxycarbonyl)methyl]-2,6'-dioxo spiro[indole-3,3'-piperidine]-1-methoxyethyl trimethylsilane as a white foam (Yield: 2.98 g, 79%).

EXAMPLE 15d

Preparation of intermediate racemic (2'R, 3R, 4'S)-6-chloro-4'-(3-chlorophenyl)-2'-isopropenyl-2,3-dihydro-1'-[(tert-butoxycarbonyl)methyl]-2-oxo-6'-thioxo spiro[indole-3,3'-piperidine]-1-methoxyethyl trimethylsilane

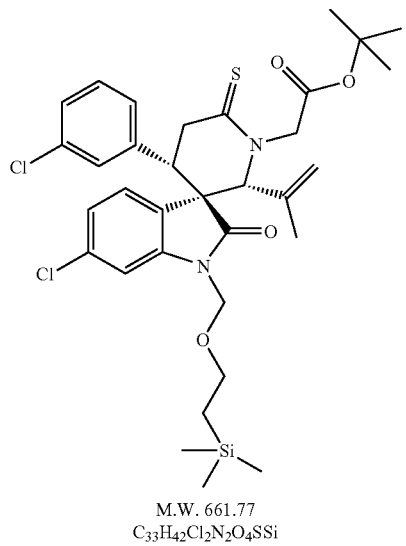

M.W. 661.77
C$_{33}$H$_{42}$Cl$_2$N$_2$O$_4$SSi

In a manner similar to the method described in example 1f racemic (2'R, 3R, 4'S)-6-chloro-4'-(3-chlorophenyl)-2'-isopropenyl-2,3-dihydro-1'-[(tert-butoxycarbonyl)methyl]-2,6'-dioxo spiro[indole-3,3'-piperidine]-1-methoxyethyl trimethylsilane (1.6 g, 2.48 mmol) prepared in example 15c was reacted with 2,4-bis-(4-methoxyphenyl)-1,3-dithia-2,4-diphosphetane 2,4-disulfide (3 g, 7.5 mmol) (Aldrich) in toluene (100 mL) at 120° C. to give racemic (2'R, 3R, 4'S)-6-chloro-4-(3-chlorophenyl)-2'-isopropenyl-2,3-dihydro-1'-[(tert-butoxycarbonyl)methyl]-2-oxo-6'-thioxo spiro[indole-3,3'-piperidine]-1-methoxyethyl trimethylsilane as a white foam (Yield 15 g, 91%).

EXAMPLE 15e

Preparation of intermediate racemic (6'R, 3R, 8'S)-6-chloro-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane

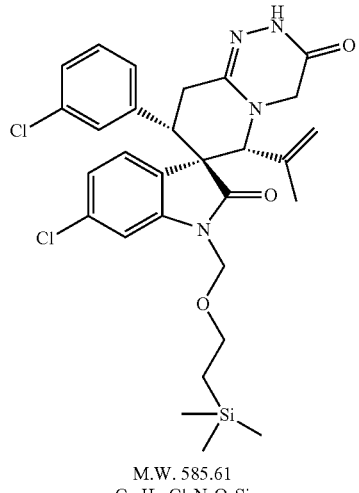

M.W. 585.61
C$_{29}$H$_{34}$Cl$_2$N$_4$O$_3$Si

In a manner similar to the method described in example 1g, racemic (2'R, 3R, 4'S)-6-chloro-4'-(3-chlorophenyl)-2'-isopropenyl-2,3-dihydro-1'-[(tert-butoxycarbonyl)methyl]-2-oxo-6'-thioxo spiro[indole-3,3'-piperidine]-1-methoxyethyl trimethylsilane (1.5 g, 2.27 mmol) prepared in example 15d was reacted with hydrazine monohydrate (9 g, ~0.1 mol) (Aldrich, 64-65%) in methanol (20 ml) in a sealed tube at 120° C. to give racemic (6'R, 3R, 8'S)-6-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane as a white solid (Yield 0.9 g, 68%).

EXAMPLE 15f

Preparation of intermediate racemic (6'R, 3R, 8'S)-6-8'-(3-chlorophenyl)-6'-isopropenyl-2'-methyl-6',7',8',9'-tetrahydro-2-oxo spiro[3H-indole-3,7-(2H-pyrido[2,1-c][1,2,4]triazin-3'-one)]-1-methoxyethyl trimethylsilane

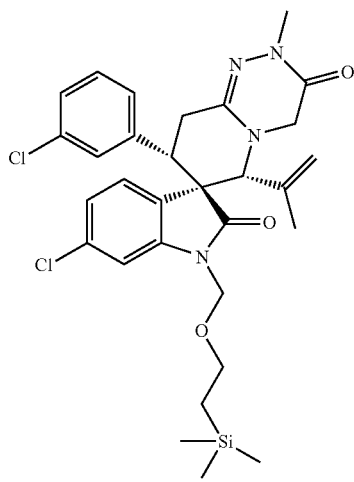

M.W. 599.64
$C_{30}H_{36}Cl_2N_4O_3Si$

In a manner similar to the method described in example 1h, racemic (6'R, 3R, 8'S)-6-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane (0.9 g, 1.54 mmol) prepared in example 15e was reacted with LiH (Aldrich) and iodomethane in N,N-dimethyl-formamide to give racemic (6'R, 3R, 8'S)-6-chloro-8'-(3-chlorophenyl)-6'-isopropenyl-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane as a off white solid (Yield 0.9 g, 97%).

EXAMPLE 15g

Preparation of racemic (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione

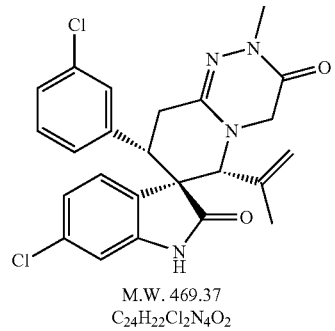

M.W. 469.37
$C_{24}H_{22}Cl_2N_4O_2$

In a manner similar to the method described in example 1i, (6'R, 3R, 8'S)-6-chloro-8'-(3-chlorophenyl)-6'-isopropenyl-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane (0.9 g, 1.5 mmol) prepared in example 15f was reacted with trifluoroacetic acid, followed by reaction with N,N'-diisopropylethylamine in methanol to give racemic (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione as a white solid (Yield 0.6 g, 85%).

HRMS (ES$^+$) m/z Calcd for $C_{24}H_{22}Cl_2N_4O_2$+H [(M+H)$^+$]: 469.1193. Found: 469.1189.

EXAMPLE 15h

Preparation of Chiral (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione

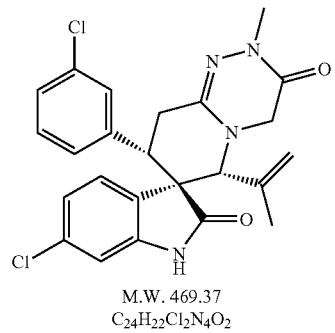

M.W. 469.37
$C_{24}H_{22}Cl_2N_4O_2$

Separation of the two enantiomers from racemic (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione (0.6 g) prepared in example 15g was conducted by chiral SFC to provide chiral (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c]

[1,2,4]triazine)]-2,3'(1H)-dione as a white solid (0.24 g, 40%) (RO5202217-000) and chiral (6'S,3S,8'R)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione as a white solid (0.24 g, 40%) (RO5202218-000).

EXAMPLE 16

Preparation of racemic (6'R, 3R, 8'S)-6-chloro-8'-(3-chlorophenyl)-6'-isopropenyl-6',7',8',9'-tetrahydro spiro[3H-indole-3,7'-(2H-pyrido[2,1-c][1,2,4]triazine)]-2,3'(1H)-dione

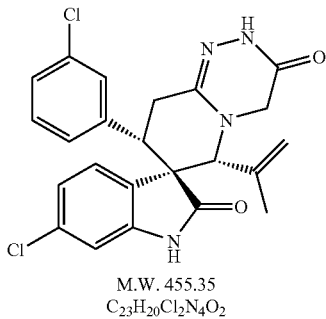

M.W. 455.35
$C_{23}H_{20}Cl_2N_4O_2$

In a manner similar to the method described in example 1i, racemic (6'R, 3R,8'S)-6-chloro-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane (24 mg, 0.04 mmol) prepared in example 15e was reacted with trifluoroacetic acid and then N,N'-diisopropylethylamine in methanol to give racemic (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (18 mg, 99%).

HRMS (ES$^+$) m/z Calcd for $C_{23}H_{20}Cl_2N_4O_2$+H[(M+H)$^+$]: 455.1036. Found: 455.1038.

EXAMPLE 17a

Preparation of intermediate racemic (2'S,3R, 4'S)-6-chloro-4'-(3-chlorophenyl)-2'-isopropenyl-2,3-dihydro-2,6'-dioxo spiro[indole-3,3'-piperidine]-1-methoxyethyl trimethylsilane

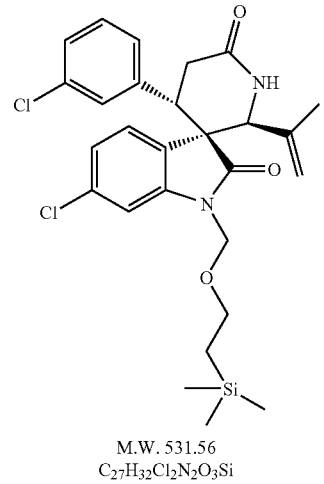

M.W. 531.56
$C_{27}H_{32}Cl_2N_2O_3Si$

In a manner similar to the method described in example 15b, E/Z-6-chloro-3-(3-chlorobenzylidene)-1-(2-trimethylsilanyl-ethoxymethyl)-1,3-dihydro-indole-2-one (420 mg, 1 mmol) prepared in example 1b was reacted with 1-isopropenyl-3-trimethylsilyoxy-2-aza-1,3-butadiene (2 g, 10.5 mmol) prepared in example 15a in toluene (10 mL) to give racemic (2'R, 3R, 4'S)-6-4'-(3-chlorophenyl)-2'-isopropenyl-2,3-dihydro-2,6'-dioxo spiro[indole-3,3'-piperidine]-1-methoxyethyl trimethylsilane as a white gum (170 mg 32%).

The other product obtained is racemic (2'S,3R, 4'S)-6-chloro-4'-(3-chlorophenyl)-2'-isopropenyl-2,3-dihydro-2,6'-dioxo spiro[indole-3,37-piperidine]-1-methoxyethyl trimethylsilane: white foam (160 mg, 30%).

EXAMPLE 17b

Preparation of intermediate racemic (2'S,3R, 4'S)-6-chloro-4-(3-chlorophenyl)-2'-isopropenyl-2,3-dihydro-1'-[(tert-butoxycarbonyl)methyl]-2,6'-dioxo spiro[indole-3,3'-piperidine]-1-methoxyethyl trimethylsilane

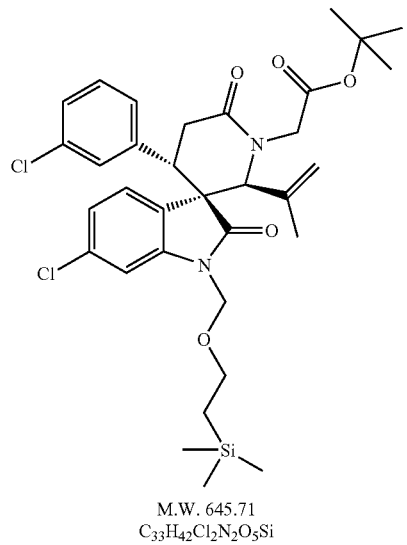

M.W. 645.71
$C_{33}H_{42}Cl_2N_2O_5Si$

In a manner similar to the method described in example 15c, racemic (2'S,3R,4'S)-6-4'-(3-chlorophenyl)-2'-isopropenyl-2,3-dihydro-2,6'-dioxo spiro[indole-3,3'-piperidine]-1-methoxyethyl trimethylsilane (160 mg, 0.3 mmol) prepared in example 17a was reacted with bromo-acetic acid tert-butyl ester and cesium carbonate in N,N-dimethyl-formamide to give racemic (2'S,3R, 4'S)-6-chloro-4'-(3-chlorophenyl)-2'-isopropenyl-2,3-dihydro-1'-[(tert-butoxycarbonyl)methyl]-2,6'-dioxo spiro[indole-3,3'-piperidine]-1-methoxyethyl trimethylsilane as a white foam (Yield: 110 mg, 56%).

EXAMPLE 17c

Preparation of intermediate racemic (2'S,3R, 4'S)-6-chloro-4'-(3-chlorophenyl)-2'-isopropenyl-2,3-dihydro-1-[(tert-butoxycarbonyl)methyl]-2-oxo-6'-thioxo spiro[indole-3,3'-piperidine]-1-methoxyethyl trimethylsilane

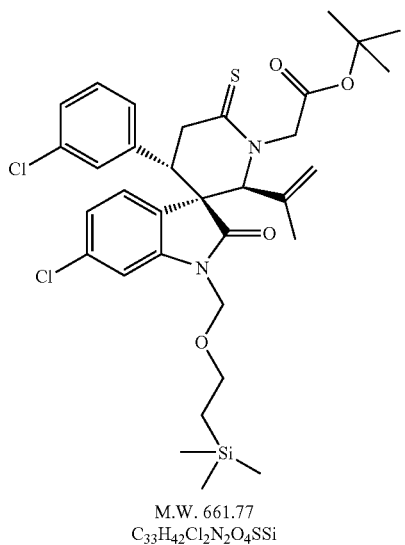

M.W. 661.77
$C_{33}H_{42}Cl_2N_2O_4SSi$

In a manner similar to the method described in example 15d racemic (2'S,3R,4'S)-4-chloro-4'-(3-chlorophenyl)-2'-isopropenyl-2,3-dihydro-1-[(tert-butoxycarbonyl)methyl]-2,6'-dioxo spiro[indole-3,3'-piperidine]-1-methoxyethyl trimethylsilane (110 mg, 0.17 mmol) prepared in example 17b was reacted with 2,4-bis-(4-methoxyphenyl)-1,3-dithia-2,4-diphosphetane 2,4-disulfide (Aldrich) in toluene at 110° C. to give racemic (2'S, 3R, 4'S)-6-chloro-4'-(3-chlorophenyl)-2'-isopropenyl-2,3-dihydro-1'-[(tert-butoxycarbonyl)methyl]-2-oxo-6'-thioxo spiro[indole-3,3'-piperidine]-1-methoxyethyl trimethylsilane as a white foam (Yield 70 mg, 62%).

EXAMPLE 17d

Preparation of intermediate racemic (6'S,3R, 8'S)-6-chloro-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane

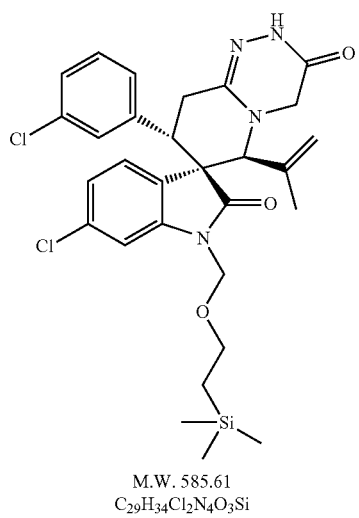

M.W. 585.61
$C_{29}H_{34}Cl_2N_4O_3Si$

In a manner similar to the method described in example 15e, racemic (2'S,3R,4'S)-6-chloro-4'-(3-chlorophenyl)-2'-isopropenyl-2,3-dihydro-1'-[(ter-butoxycarbonyl)methyl]-2-oxo-6'-thioxo spiro[indole-3,3'-piperidine]-1-methoxyethyl trimethylsilane (70 mg, 0.11 mmol) prepared in example 17c was reacted with hydrazine monohydrate (6 g, 2.1 mmol) (Aldrich, 64-65%) in methanol (2 ml) in a sealed tube at 120° G for 24 h to give racemic (6'S,3R, 8'S)-6-chloro-8'-(3-chlorophenyl)-6'-isopropenyl-6',7',8',9'-tetrahydro-2-oxo spiro [3H-indole-3,7'-(2H-pyrido[2,1-c][1,2,4]triazin-3'-one)]-1-methoxyethyl trimethylsilane as a white solid (Yield 33 mg, 51%).

EXAMPLE 17e

Preparation of racemic (6'S,3R, 8'R)-6-chloro-8'-(3-chlorophenyl)-6'-isopropenyl-6',7',8',9'-tetrahydro spiro[3H-indole-3,7'-(2H-pyrido[2,1-c][1,2,4]triazine)]-2,3'(1H)-dione

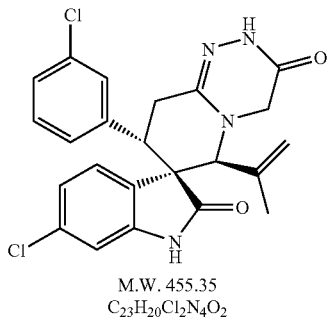

M.W. 455.35
$C_{23}H_{20}Cl_2N_4O_2$

In a manner similar to the method described in example 16, racemic (6'S,3R,8'S)-6-chloro-8'-(3-chlorophenyl)-6'-isopropenyl-6',7',8',9'-tetrahydro-2-oxo spiro[3H-indole-3,7'-(2H-pyrido[2,1-c][1,2,4]triazin-3'-one)]-1-methoxyethyl trimethylsilane (33 mg, 0.056 mmol) prepared in example 17d was reacted with trifluoroacetic acid and then N,N'-diisopropylethylamine in methanol at 100° C. to give racemic (6'S,3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione as a white solid (21 mg, 82%).

HRMS (ES⁺) m/z Calcd for $C_{23}H_{20}Cl_2N_4O_2$+H [(M+H)⁺]: 455.1036. Found: 455.1036.

EXAMPLE 18a

Preparation of intermediate 2-allyloxy-5-iodo-benzaldehyde

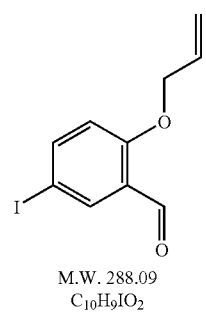

M.W. 288.09
$C_{10}H_9IO_2$

To a solution of 2-hydroxy-5-iodo-benzaldehyde (16 g, 64.5 mmol) (Aldrich) in N,N-dimethylformamide (100 mL) was added $K_2CO_3$ (16 g, 115 mmo) and allyl bromide (20 g, 165 mmol) (Aldrich). The reaction mixture was stirred at 100° C. for 3 h, then cooled to room temperature and poured into water, extracted with ethyl acetate. The organic layers were combined, washed with water, brine, dried over $MgSO_4$, filtered and concentrated to give 2-allyloxy-5-iodo-benzaldehyde as a white solid (Yield: 18g, 97%).

EXAMPLE 18b

Preparation of intermediate 1-(2-allyloxy-5-iodo-phenyl)-3-trimethylsilyoxy-2-aza-1,3-butadiene

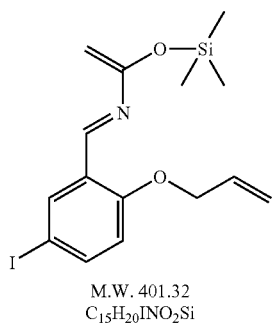

M.W. 401.32
$C_{15}H_{20}INO_2Si$

In a manner similar to the method described in example 1c 2-allyloxy-5-iodo-benzaldehyde (19 g, 65 mmol) prepared in example 18a was used as the starting material in place of 5-fluoro-2-methyl-benzaldehyde to react with 1,1,1,3,3,3-hexamethyldisilazane (11 g, 68 mmol), n-butyllithium (2.5 M, 17 mL, 68 mmol), trimethylsilyl chloride (7.4 g, 68 mmol), triethylamine (9.4 g, 92 mmol) and acetyl chloride (7.2 g, 92 mmol) to give 1-(2-allyloxy-5-iodo-phenyl)-3-trimethylsilyoxy-2-aza-1,3-butadiene and used for the next step without further purification.

EXAMPLE 18c

Preparation of intermediate racemic (2'R, 3R, 4'S)-2'-(2-allyloxy-5-iodo-phenyl)-6-chloro-4'-(3-chlorophenyl)-2,3-dihydro-2,6'-dioxo spiro[indole-3,3'-piperidine]-1-methoxyethyl trimethylsilane

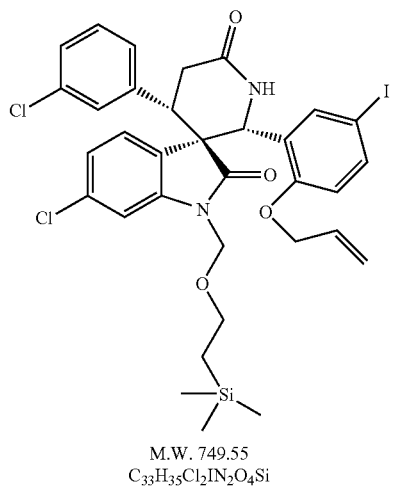

M.W. 749.55
$C_{33}H_{35}Cl_2IN_2O_4Si$

In a manner similar to the method described in example 1d, E/Z-6-chloro-3-(3-chlorobenzylidene)-1-(2-trimethylsilanyl-ethoxymethyl-1,3-dihydro-indole-2-one (6 g, 15 mmol) prepared in example 1b was reacted with 1-(2-allyloxy-5-iodo-phenyl)-3-trimethylsilyoxy-2-aza-1,3-butadiene (26 g, 65 mmol) prepared in example 18b in toluene (100 mL) to give racemic (2'R, 3R, 4'S)-2'-(2-allyloxy-5-iodo-phenyl)-6-chloro-4'-(3-chlorophenyl)-2,3-dihydro-2,6'-dioxo spiro[indole-3,3'-piperidine]-1-methoxyethyl trimethylsilane as a white foam (5 g, 44%)

EXAMPLE 18d

Preparation of intermediate racemic (2'R, 3R, 4'S)-2'-(2-allyloxy-5-iodo-phenyl)-1-[(tert-butoxycarbonyl)methyl]-6-chloro-4'-(3-chlorophenyl)-2,3-dihydro-2,6'-dioxo spiro[indole-3,3'-piperidine]-1-methoxyethyl trimethylsilane

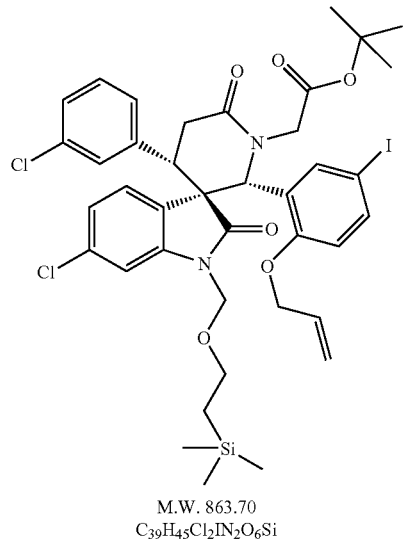

M.W. 863.70
$C_{39}H_{45}Cl_2IN_2O_6Si$

In a manner similar to the method described in example 1e, racemic (2'R, 3R,4'S)-2'-(2-allyloxy-5-iodo-phenyl)-6-chloro-4'-(3-chlorophenyl)-2,3-dihydro-2,6'-dioxo spiro[indole-3,3'-piperidine]-1-methoxyethyl trimethylsilane (5 g, 6.6 mmol) prepared in example 18c was reacted with bromoacetic acid tert-butyl ester and cesium carbonate in N,N-dimethyl-formamide to give racemic (2'R, 3R, 4'S)-2'-(2-allyloxy-5-iodo-phenyl)-1'-[(tert-butoxycarbonyl)methyl]-6-chloro-4'-(3-chlorophenyl)-2,3-dihydro-2,6'-dioxo spiro[indole-3,3'-piperidine]-1-methoxyethyl trimethylsilane as a white foam (Yield: 2.8 g, 49%).

EXAMPLE 18e

Preparation of intermediate racemic (2'R, 3R, 4'S)-2'-(2-allyloxy-5-iodo-phenyl)-1'-[(tert-butoxycarbonyl)methyl]-6-chloro-4'-(3-chlorophenyl)-2,3-dihydro-2-dioxo-6'-thioxo spiro[indole-3,3'-piperidine]-1-methoxyethyl trimethylsilane

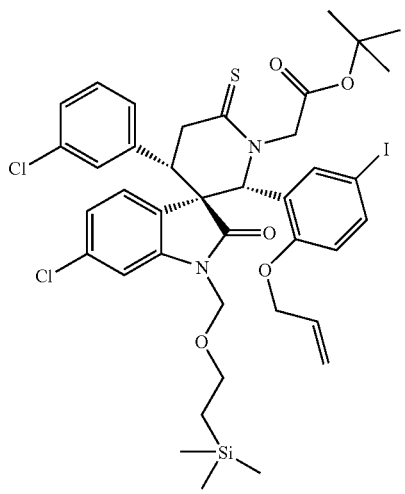

M.W. 879.76
C$_{39}$H$_{45}$Cl$_2$IN$_2$O$_5$SSi

In a manner similar to the method described in example 1f, racemic (2'R, 3R,4'S)-2'-(2-allyloxy-5-iodo-phenyl)-1'-[(tert-butoxycarbonyl)methyl]-6-chloro-4 (3 chlorophenyl)-2,3-dihydro-2,6'-dioxo spiro[indole-3,3'-piperidine]-1-methoxyethyl trimethylsilane (2.8 g, 3.3 mmol) prepared in example 18d was reacted with 2,4-bis-(4-methoxyphenyl)-1,3-dithia-2,4-diphosphetane 2,4-disulfide (2 g, 5 mmol) (Aldrich) in toluene (50 mL) at 120° C. to give racemic (2'R, 3R, 4'S)-2'-(2-allyloxy-5-iodo-phenyl)-1'-[(tert-butoxycarbonyl)methyl]-6-chloro-4'-(3-chlorophenyl)-2,3-dihydro-2-dioxo-6'-thioxo spiro[indole-3,3'-piperidine]-1-methoxyethyl trimethylsilane as a white foam (Yield 1.8 g, 62%).

EXAMPLE 18f

Preparation of intermediate racemic (6'R, 3R, 8'S)-6'-(2-allyloxy-5-iodo-phenyl)-6-chloro-8'-(3-chlorophenyl)-6',7',8',9'-tetrahydro-2-oxo spiro[3H-indole-3,7'-(2H-pyrido[2,1-c][1,2,4]triazin-3'-one)]-1-methoxyethyl trimethylsilane

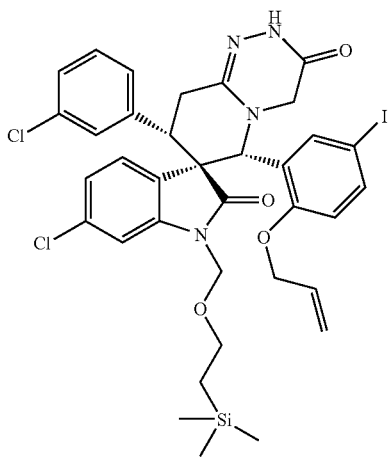

M.W. 803.61
C$_{35}$H$_{37}$Cl$_2$IN$_4$O$_4$Si

In a manner similar to the method described in example 1g, racemic (2'R, 3R,4'S)-2'-(2-allyloxy-5-iodo-phenyl)-1'-[(tert-butoxycarbonyl)methyl]-6-chloro-4'-(3-chlorophenyl)-2,3-dihydro-2-dioxo-6'-thioxo spiro[indole-3,3'-piperidine]-1-methoxyethyl trimethylsilane (1.8 g, 2.0 mmol) prepared in example 18e was reacted with hydrazine monohydrate (8 g, ~89 mmol) (Aldrich, 64-65%) in methanol (20 ml) in a sealed tube at 120° C. to give racemic (6'R, 3R, 8'S)-6'-(2-allyloxy-5-iodo-phenyl)-6-chloro-8'-(3-chlorophenyl)-6',7',8',9'-tetrahydro-2-oxo spiro[3H-indole-3,7'-(2H-pyrido[2,1-c][1,2,4]triazin-3'-one)]-1-methoxyethyl trimethylsilane as a white solid (Yield 0.73 g, 45%).

EXAMPLE 18g

Preparation of intermediate racemic (6'R, 3R, 8'S)-6'-(2-allyloxy-5-Iodo-phenyl)-6-chloro-8'-(3-chlorophenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane

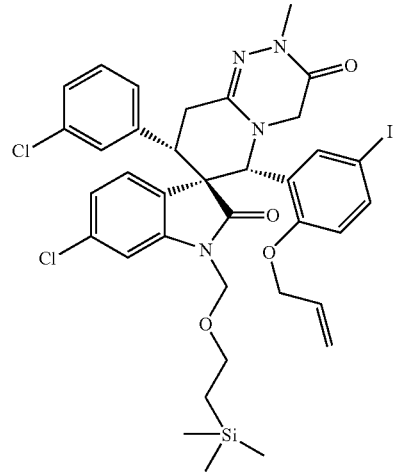

M.W. 817.63
C$_{36}$H$_{39}$Cl$_2$IN$_4$O$_4$Si

In a manner similar to the method described in example 1h, racemic (6'R, 3R,8'S)-6'-(2-allyloxy-5-iodo-phenyl)-6-chloro-8'-(3-chlorophenyl)-6',7',8',9'-tetrahydro-2-oxo spiro[3H-indole-3,7'-(2H-pyrido[2,1-c][1,2,4]triazin-3'-one)]-1-methoxyethyl trimethylsilane (0.73 g, 0.9 mmol) prepared in example 18f was reacted with LiH (Aldrich) and iodomethane in N,N-dimethyl-formamide to give racemic (6'R, 3R, 8'S)-6'-(2-allyloxy-5-iodo-phenyl)-6-chloro-8'-(3-chlorophenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane as a white solid (Yield 0.66 g, 90%).

EXAMPLE 18g

Preparation of racemic (6'R, 3R, 8'S)-6'-(2-allyloxy-5-iodo-phenyl)-6-chloro-8'-(3-chlorophenyl)-2'-methyl-6',7',8',9'-tetrahydro spiro[3H-indole-3,7'-(2H-pyrido[2,1-c][1,2,4]triazine)]-2,3'(1H)-dione

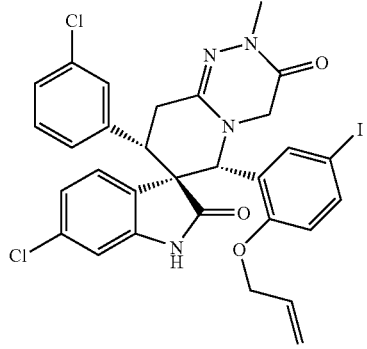

M.W. 687.37
$C_{30}H_{25}Cl_2IN_4O_3$

In a manner similar to the method described in example 1i, (6'R, 3R, 8'S)-6'-(2-allyloxy-5-iodo-phenyl)-6-chloro-8'-(3-chlorophenyl)-2'-methyl-6',7',8',9'-tetrahydro-2-oxo spiro[3H-indole-3,7'-(2H-pyrido[2,1-c][1,2,4]triazin-3'-one)]-1-methoxyethyl trimethylsilane (0.41 g, 0.5 mmol) prepared in example 18g was reacted with trifluoroacetic acid, followed by reaction with N,N'-diisopropylethylamine in methanol to give racemic (6'R, 3R, 8'S)-6'-(2-allyloxy-5-iodo-phenyl)-6-chloro-8'-(3-chlorophenyl)-2'-methyl-6',7',8',9'-tetrahydro spiro[3H-indole-3,7'-(2H-pyrido[2,1-c][1, 2,4]triazine)]-2,3'(1H)-dione as a white solid (Yield 0.31 g, 90%).

HRMS (ES$^+$) m/z Calcd for $C_{30}H_{25}Cl_2IN_4O_3$+H [(M+H)$^+$]: 687.0421. Found: 687.0421

EXAMPLE 19

Preparation of racemic (6'R, 3R, 8'S)-6-chloro-8'-(3-chlorophenyl)-6'-(5-ethynyl-2-hydroxy-phenyl)-2'-methyl-6',7',8',9'-tetrahydro spiro[3H-indole-3,7'-(2H-pyrido[2,1-c][1,2,4]triazine)]-2,3'(1H)-dione

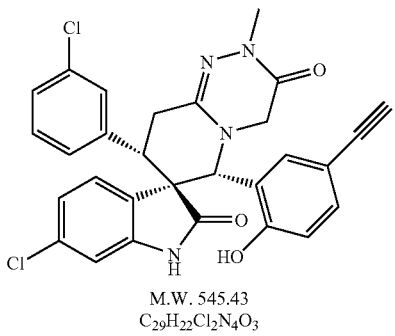

M.W. 545.43
$C_{29}H_{22}Cl_2N_4O_3$

To a solution of racemic (6'R, 3R, 8'S)-6-(2-allyloxy-5-iodo-phenyl)-6-chloro-8'-(3-chlorophenyl)-2'-methyl-6',7', 8',9'-tetrahydro spiro[3H-indole-3,7'-(2H-pyrido[2,1-c][1,2, 4]triazine)]-2,3'(1H)-dione (70 mg, 0.1 mmol) prepared in example 18g in anhydrous tetrahydrofuran (14 mL) was added trimethylsilyl acetylene (20 mg, 0.2 mmol) (Alfa), CuI (39 mg, 0.2 mmol) (Aldrich), and triethylamine (21 mg, 0.2 mmol). After the reaction mixture was degassed under nitrogen for 10 min, bis(triphenylphosphine)palladium(II) dichloride (14 mg, 0.02 mmol) (Strem) was added and the reaction mixture was heated at 100° C. under nitrogen for 3 h. The reaction mixture was cooled to room temperature and diluted with water, extracted with ethyl acetate. The organic layers were combined, washed with water, brine, dried over MgSO$_4$, filtered and concentrated.

To the residue was added methanol (2 mL) and added aqueous NaOH (1 N, 2 ml, 20 mmol). The reaction mixture was stirred at room temperature for 1 h. The solvent was removed and the residue was diluted with water and extracted with ethyl acetate. The organic layers were combined, washed with water, brine, dried over MgSO$_4$, filtered and concentrated. The residue was purified with chromatography (EtOAc) to give racemic (6'R, 3R, 8'S)-6-chloro-8'-(3-chlorophenyl)-6'-(5-ethynyl-2-hydroxy-phenyl)-2'-methyl-6',7', 8',9'-tetrahydro spiro[3H-indole-3,7'-(2H-pyrido[2,1-c][1,2, 4]triazine)]-2,3'(1H)-dione as a off white solid (Yield 21 mg, 38%).

HRMS (ES$^+$) m/z Calcd for $C_{29}H_{22}Cl_2N_4O_3$+H [(M+H)$^+$]: 545.1142. Found: 545.1142.

EXAMPLE 20

Preparation of racemic (6'R, 3R, 8'S)-6-chloro-8'-(3-chlorophenyl)-6'-[2-(2,3-dihydroxy-propoxy)-5-iodo-phenyl)-2'-methyl-6',7',8',9'-tetrahydro spiro[3H-indole-3,7'-(2H-pyrido[2,1-c][1,2,4]triazine)]-2,3'(1H)-dione

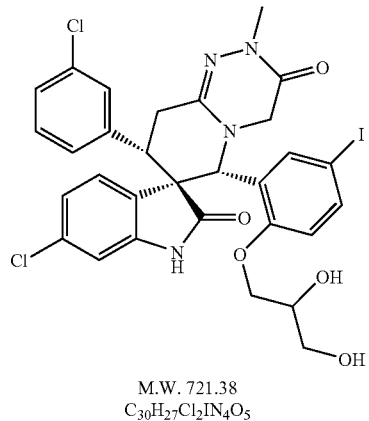

M.W. 721.38
$C_{30}H_{27}Cl_2IN_4O_5$

To a solution of racemic (6'R, 3R, 8'S)-6-chloro-8'-(3-chlorophenyl)-6'-(2-hydroxy-5-iodo-phenyl)-2'-methyl-6',7',8', 9'-tetrahydro spiro[3H-indole-3,7'-(2H-pyrido[2,1-c][1,2,4]triazine)]-2,3'(1H)-dione (118 mg, 0.17 mmol) prepared in example 18g was added 0504 (4% in H$_2$O, 0.22 g, 0.03 mmol), N-methylmorpholine N-oxide (40 mg, 0.34 mmol) (Aldrich). The reaction mixture was stirred at room temperature for 18 h. The mixture was concentrated, and the residue was purified by chromatography (EtOAc:MeOH=9:1) to give racemic (6'R, 3R, 8'S)-6-chloro-8'-(3-chlorophenyl)-6'-[2-(2, 3-dihydroxy-propoxy)-5-iodo-phenyl)-2'-methyl-6',7',8',9'-tetrahydro spiro[3H-indole-3,7'-(2H-pyrido[2,1-c][1,2,4]triazine)]-2,3'(1H)-dione as a white solid (Yield 80 mg, 65%)

HRMS (ES⁺) m/z Calcd for $C_{30}H_{27}Cl_{21}N_4O+H$ [(M+H)⁺]: 721.0476. Found: 721.0478

EXAMPLE 21

Preparation of racemic (6'R, 3R, 8'S)-6-chloro-8'-(3-chlorophenyl)-6'-[2-(2,3-dihydroxy-propoxy)-5-ethynyl-phenyl)-2'-methyl-6',7',8',9'-tetrahydro spiro [3H-indole-3,7'-(2H-pyrido[2,1-c][1,2,4]triazine)]-2,3'(1H)-dione

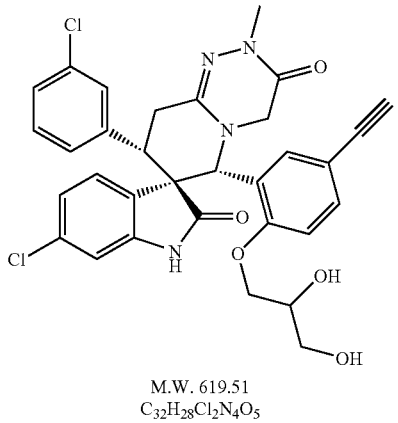

M.W. 619.51
$C_{32}H_{28}Cl_2N_4O_5$

To a solution of racemic (6'R, 3R, 8'S)-6-chloro-8'-(3-chlorophenyl)-6'-[2-(2,3-dihydroxy-propoxy)-5-iodo-phenyl)-2'-methyl-6',7',8',9'-tetrahydro spiro[3H-indole-3,7'-(2H-pyrido[2,1-c][1,2,4]triazine)]-2,3'(1H)-dione as a white solid (80 mg, 0.11 mmol) prepared in example 20 in anhydrous tetrahydrofuran (20 mL) was added trimethylsilyl acetylene (22 mg, 0.22 mmol) (Alfa), CuI (42 mg, 0.22 mmol) (Aldrich), and triethylamine (22 mg, 0.22 mmol). After the reaction mixture was degassed under nitrogen for 10 min, bis(triphenylphosphine)palladium(II) dichloride (15 mg, 0.02 mmol) (Strem) was added and the reaction mixture was heated at 100° C. under nitrogen for 1 h. The reaction mixture was cooled to room temperature and diluted with water, extracted with ethyl acetate. The organic layers were combined, washed with water, brine, dried over $MgSO_4$, filtered and concentrated.

To the residue was added methanol (10 mL) and added aqueous NaOH (1 N, 1 ml, 10 mmol). The reaction mixture was stirred at room temperature for 1 h. The solvent was removed and the residue was diluted with water and extracted with ethyl acetate. The organic layers were combined, washed with water, brine, dried over $MgSO_4$, filtered and concentrated. The residue was purified with chromatography (EtOAc) to give racemic (6'R, 3R, 8'S)-6-chloro-8'-(3-chlorophenyl)-6'-[2-(2,3-dihydroxy-propoxy)-5-ethynyl-phenyl)-2'-methyl-6',7',8',9'-tetrahydro spiro[3H-indole-3,7'-(2H-pyrido[2,1-c][1,2,4]triazine)]-2,3'(1H)-dione as a off white solid (Yield 51 mg, 64%).

HRMS (ES⁺) m/z Calcd for $C_{32}H_{28}Cl_2N_4O_5+H$ [(M+H)⁺]: 619.1510. Found: 619.1505.

EXAMPLE 22

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 mM Eu-labeled anti-GST-antibody (PerkinElmerWallac), 0.2% bovine serum albumin (BSA), 1 mM dithiothreitol (DTT) and 20 mM Tris-borate seine (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solutions), in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma, Chemical Co.

$IC_{50}$'s showing the biological activity of this invention exhibit activities less than about 10 μM.

Examples of the biological values are as follows:

| Example No. | $IC_{50}$, μM |
| --- | --- |
| 1i | 0.191 |
| 5b | 0.1001 |
| 7b | 0.89 |
| 11c | 0.293 |
| 18g | 0.272 |

What is claimed:
1. A compound of the formula

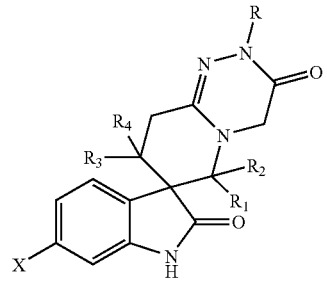

I wherein
X is selected from the group consisting of hydrogen, halogen, cyano, nitro, ethynyl, cyclopropyl, methyl, ethyl, isopropyl, methoxy and vinyl,
one of $R_1$ and $R_2$ is selected from the group consisting of lower alkyl substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, one of $R_3$ and $R_4$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl; and substituted cycloalkenyl and the other is hydrogen, R is selected from the group consisting of hydrogen, lower alkyl and substituted lower alkyl or a pharmaceutically acceptable salt thereof.

2. A compound of the formula

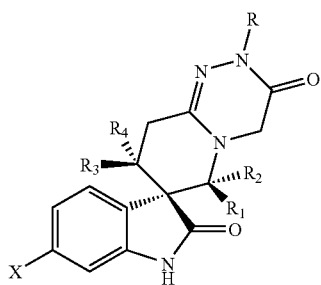

II wherein

X is selected from the group consisting of hydrogen, halogen, cyano, nitro, ethynyl, cyclopropyl, methyl, ethyl, isopropyl methoxy and vinyl, one of $R_1$ and $R_2$ is selected from the group consisting of lower alkyl substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, one of $R_3$ and $R_4$ is selected from the group consisting of lower alkyl substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, R is selected from the group consisting of hydrogen, lower alkyl and substituted lower alkyl, or a pharmaceutically acceptable salt thereof.

3. The compound of claim 2 wherein

X is selected from the group consisting of hydrogen, halogen, cyano, nitro, ethynyl, cyclopropyl, methyl, ethyl, isopropyl, methoxy and vinyl, $R_1$ is hydrogen, $R_3$ is hydrogen, $R_2/R_4$ is independently selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl and R is selected from the group consisting of hydrogen, lower alkyl and substituted lower alkyl.

4. The compound of claim 3 wherein

X is chlorine or bromine, $R_4$ is a substituted phenyl or substituted heteroaryl with the substituted phenyl or substituted heteroaryl selected from group consisting of

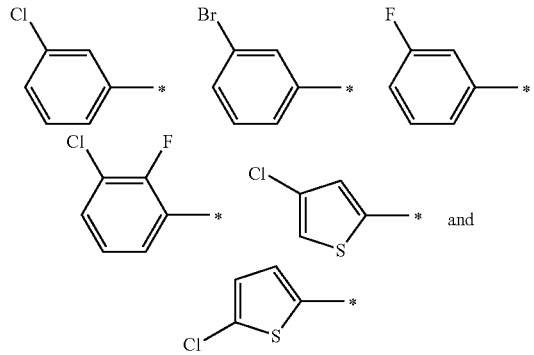

and $R_2$ is independently selected from the group consisting of lower alkenyl, substituted lower alkenyl, aryl, substituted aryl, heteroaryl, substituted heteroaryl, cycloalkenyl and substituted cycloalkenyl.

5. A compound of claim 1 selected from the group consisting of racemic (6'R, 3R, 8'S)-6-chloro-8'-(3-chlorophenyl)-6'-(5-fluoro-2-methylphenyl)-2'-methyl-6',7',8',9'-tetrahydro spiro[3H-indole-3,7'-(2H-pyrido[2,1-c][1,2,4]triazine)]-2,3'(1H)-dione;

Chiral (6'R, 3R, 8'S)-6-8'-(3-chlorophenyl)-6'-(5-fluoro-2-methylphenyl)-2'-methyl-6',7',8',9'-tetrahydro spiro [3H-indole-3,7'-(2H-pyrido[2,1-c][1,2,4]triazine)]-2,3' (1H)-dione, racemic (6'R, 3R, 8'S)-6-8'-(3-chlorophenyl)-6'-(5-fluoro-2-methylphenyl)-6',7',8',9'-tetrahydro spiro[3H-indole-3,7'-(2H-pyrido[2,1-c][1,2,4]triazine)]-2,3'(1H)-dione, racemic (6'R, 3R, 8'S)-6-chloro-8'-(3-chlorophenyl)-6'-(1-methylene-propyl)-2'-methyl-6',7',8',9'-tetrahydro spiro [3H-indole-3,7'-(2H-pyrido[2,1-c][1,2,4]triazine)]-2,3' (1H)-dione, Chiral (6'R, 3R, 8'S)-6-chloro-8'-(3-chlorophenyl)-6'-(1-methylene-propyl)-2'-methyl-6',7',8',9'-tetrahydro spiro [3H-indole-3,7'-(2H-pyrido[2,1-c][1,2,4]triazine)]-2,3' (1H)-dione, racemic (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione, Chiral (6'R, 3R, 8'S)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione, racemic (6'R, 3R, 8'S)-6-8'-(3-chlorophenyl)-2'-(3-dimethylaminopropyl)-6'-(1-methylene-propyl)-6',7',8',9'-tetrahydro spiro[3H-indole-3,7'-(2H-pyrido[2,1-c][1,2,4]triazine)]-2,3'(1H)-dione, racemic (6'R, 3R, 8'S)-6-chloro-8'-(3-chlorophenyl)-2'-(2-methoxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione and racemic (6'R, 3R, 8'S)-2'-(2-acetoxyethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione.

6. A compound of claim 1 selected from the group consisting of
- racemic (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1,2,4]triazine)]-2,3'(1H)-dione,
- Chiral (6'R, 3R, 8'S)-6-chloro-8'-(3-chlorophenyl)-2'-(2-hydroxyethyl)-6'-(1-methylene-propyl)-6',7',8',9'-tetrahydro spiro[3H-indole-3,7'-(2H-pyrido[2,1-c][1, 2, 4]triazine)]-2,3'(1H)-dione,
- racemic (6'R, 3R, 8'S)-2'-(2-acetylaminoethyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-chloro-8'-(3-chlorophenyl)-2'-(2-hydroxycarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-8'-(3-chlorophenyl)-2'-(2-fluorocarbonyl-methyl)-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-8'-(3-chlorophenyl)-2'-[(2-hydroxyethylamino)carbonyl-methyl]6'-(1-methylene-propyl)-6',7',8',9'-tetrahydro spiro[3H-indole-3,7'-(2H-pyrido[2,1-c][1,2,4]triazine)]-2,3'(1H)-dione,
- Chiral (6'R, 3R, 8'S)-6-chloro-8'-(3-chlorophenyl)-2'-[(2-hydroxyethylamino)carbonyl-methyl]N'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-8'-(3-chlorophenyl)-2'-[(2-cyclopropylamino)carbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione,
- Chiral (6'R, 3R, 8'S)-6-chloro-8'-(3-chlorophenyl)-2'-[(2-cyclopropylamino)carbonyl-methyl]6'-(1-methylene-propyl)-6',7',8',9'-tetrahydro spiro[3H-indole-3,7'-(2H-pyrido[2,1-c][1,2,4]triazine)]-2,3'(1H)-dione and
- racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione.

7. A compound of claim 1 selected from the group consisting of
- racemic (6'R, 3R, 8'S)-2'-(2-aminocarbonyl-methyl)-6-chloro-8'-(3-chlorophenyl)-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-chloro-8'-(3-chlorophenyl)-2'-[(1-methanesulfonyl-piperidin-4-yl)aminocarbonyl-methyl]-6'-(1-methylene-propyl)-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-chloro-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione,
- Chiral (6'R, 3R, 8'S)-6-8'-(3-chlorophenyl)-6'-isopropenyl-2'-methyl-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-8'-(3-chlorophenyl)-6'-isopropenyl-6',7',8',9'-tetrahydro spiro[3H-indole-3,7'-(2H-pyrido[2,1-c][1,2,4]triazine)]-2,3'(1H)-dione,
- racemic (6'S, 3R, 8'R)-6-chloro-8'-(3-chlorophenyl)-6'-isopropenyl-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6'-(2-allyloxy-5-iodo-phenyl)-6-chloro-8'-(3-chlorophenyl)-2'-methyl-6',7',8',9'-tetrahydro spiro[3H-indole-3,7'-(2H-pyrido[2,1-c][1,2,4]triazine)]-2,3'(1H)-dione,
- racemic (6'R, 3R, 8'S)-6-chloro-8'-(3-chlorophenyl)-6'-(5-ethynyl-2-hydroxy-phenyl)-2'-methyl-6',7',8',9'-tetrahydro spiro[3H-indole-3,7'-(2H-pyrido[2,1-c][1,2,4]triazine)]-2,3'(1H)-dion,
- racemic (6'R, 3R, 8'S)-6-8'-(3-chlorophenyl)-6'-[2-(2,3-dihydroxy-propoxy)-5-iodo-phenyl]-2'-methyl-6',7',8',9'-tetrahydro spiro[3H-indole-3,7'-(2H-pyrido[2,1-c][1,2,4]triazine)]-2,3'(1H)-dione and
- racemic (6'R, 3R, 8'S)-6-chloro-8'-(3-chlorophenyl)-6'-[2-(2,3-dihydroxy-propoxy)-5-ethynyl-phenyl]-2'-methyl-6',7',8',9'-tetrahydro spiro[3H-indole-3,7'-(2H-pyrido[2,1-c][1,2,4]triazine)]-2,3'(1H)-dione.

8. A pharmaceutical formulation comprising a compound of the formula

II wherein
- X is selected from the group consisting of hydrogen, halogen, cyano, nitro, ethynyl, cyclopropyl, methyl, ethyl, isopropyl, methoxy and vinyl,
- one of $R_1$ and $R_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
- one of $R_3$ and $R_4$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen,
- R is selected from the group consisting of hydrogen, lower alkyl and substituted lower alkyl,
- or a pharmaceutically acceptable salt thereof together with a pharmaceutically acceptable excipient.

* * * * *

UNITED STATES PATENT AND TRADEMARK OFFICE
CERTIFICATE OF CORRECTION

PATENT NO. : 7,834,179 B2  
APPLICATION NO. : 12/101206  
DATED : November 16, 2010  
INVENTOR(S) : Jin-Jun Liu et al.

Page 1 of 2

It is certified that error appears in the above-identified patent and that said Letters Patent is hereby corrected as shown below:

Column 62, Line 30, please delete
- "Chiral (6'R, 3R, 8'S)-6-8'-(3-chlorophenyl)-6'-(5-fluoro-2-"
- and insert
-- Chiral (6'R, 3R, 8'S)-6-chloro-8'-(3-chlorophenyl)-6'-(5-fluoro-2- --

Column 62, Line 35, please delete
- "racemic (6'R, 3R, 8'S)-6-8'-(3-chlorophenyl)-6'-(5-fluoro-"
- and insert
-- racemic (6'R, 3R, 8'S)-6-chloro-8'-(3-chlorophenyl)-6'-(5-fluoro- --

Column 62, Line 55, please delete
- "racemic (6'R, 3R, 8'S)-6-8'-(3-chlorophenyl)-2'-(3-dim-"
- and insert
-- racemic (6'R, 3R, 8'S)-6-chloro-8'-(3-chlorophenyl)-2'-(3-dim- --

Column 63, Line 19, please delete
- "racemic (6'R, 3R, 8'S)-6-8'-(3-chlorophenyl)-2'-(2-fluoro-"
- and insert
-- racemic (6'R, 3R, 8'S)-6-chloro-8'-(3-chlorophenyl)-2'-(2-fluoro- --

Column 63, Line 23, please delete
- "racemic (6'R, 3R, 8'S)-6-8'-(3-chlorophenyl)-2'-(2-hy-"
- and insert
-- racemic (6'R, 3R, 8'S)-6-chloro-8'-(3-chlorophenyl)-2'-(2-hy- --

Column 63, Line 31, please delete
- "racemic (6'R, 3R, 8'S)-6-8'-(3-chlorophenyl)-2'-(2-cyclo-"
- and insert
-- racemic (6'R, 3R, 8'S)-6-chloro-8'-(3-chlorophenyl)-2'-(2-cyclo- --

Signed and Sealed this  
Twenty-second Day of February, 2011

David J. Kappos  
*Director of the United States Patent and Trademark Office*

Column 64, Line 1, please delete
- "chiral (6'R, 3R, 8'S)-6-8'-(3-chlorophenyl)-6'-isoprope-"
- and insert
-- Chiral (6'R, 3R, 8'S)-6-chloro-8'-(3-chlorophenyl)-6'-isoprope --

Column 64, Line 4, please delete
- "racemic (6'R, 3R, 8'S)-6-8'-(3-chlorophenyl)-6'-isoprope-"
- and insert
-- racemic (6'R, 3R, 8'S)-6-chloro-8'-(3-chlorophenyl)-6'-isoprope- --

Column 64, Line 18, please delete
- "racemic (6'R, 3R, 8'S)-6-8'-(3-chlorophenyl)-6'-[2-(2,3-"
- and insert
-- racemic (6'R, 3R, 8'S)-6-chloro-8'-(3-chlorophenyl)-6'-[2-2,3 --